United States Patent
Van Etten et al.

(10) Patent No.: US 10,450,572 B2
(45) Date of Patent: Oct. 22, 2019

(54) ANDROGEN RECEPTOR VARIANT INHIBITORS AND METHODS OF USING

(71) Applicant: Regents of the University of Minnesota, Minneapolis, MN (US)

(72) Inventors: Jamie Lynn Van Etten, Minneapolis, MN (US); Scott M. Dehm, Rochester, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/675,072

(22) Filed: Aug. 11, 2017

(65) Prior Publication Data

US 2018/0119153 A1    May 3, 2018

Related U.S. Application Data

(60) Provisional application No. 62/374,482, filed on Aug. 12, 2016.

(51) Int. Cl.
| | |
|---|---|
| *C07H 21/02* | (2006.01) |
| *C07H 21/04* | (2006.01) |
| *A61K 48/00* | (2006.01) |
| *C12N 15/113* | (2010.01) |
| *A61K 31/713* | (2006.01) |
| *A61P 35/00* | (2006.01) |
| *A61K 45/06* | (2006.01) |

(52) U.S. Cl.
CPC ........ *C12N 15/1138* (2013.01); *A61K 31/713* (2013.01); *A61K 45/06* (2013.01); *A61P 35/00* (2018.01); *C12N 2310/11* (2013.01); *C12N 2310/314* (2013.01); *C12N 2310/3233* (2013.01); *C12N 2310/3513* (2013.01); *C12N 2320/31* (2013.01); *C12N 2320/33* (2013.01)

(58) Field of Classification Search
CPC .... C12N 15/113; C12N 15/111; A61K 31/713
See application file for complete search history.

(56) References Cited

U.S. PATENT DOCUMENTS

2015/0238627 A1* 8/2015 Leger .................... C12N 15/113
                                                            514/20.9

FOREIGN PATENT DOCUMENTS

WO    WO 2004/005458 A2 *  1/2004 ........... C12N 15/111
WO    WO 2004/085621 A2 * 10/2004 ........... C12N 15/111

OTHER PUBLICATIONS

Stanzl et al. (Acc Chem Res, 2013, 46(12), pp. 1-18).*
Beer et al., "Enzalutamide in Metastatic Prostate Cancer before Chemotherapy," *N Engl J Med.*, 371:424-433, 2014.
Cerami et al., "The cBio Cancer Genomics Portal: An Open Platform for Exploring Multidimensional Cancer Genomics Data," *Cancer Discov.*, 2(5):401-404, May 2012.
Chan et al., "Androgen Receptor Splice Variants Activate Androgen Receptor Target Genes and Support Aberrant Prostate Cancer Cell Growth Independent of Canonical Androgen Receptor Nuclear Localization Signal," *J Biol Chem.*, 287:19736-19749, 2012.
Chan et al., "CPSF30 and Wdr33 directly bind to AAUAAA in mammalian mRNA 3' processing," *Genes Dev.*, 28:2370-2380, 2014.
Dehm et al., "Alternatively spliced androgen receptor variants," Endocr Relat Cancer., 18(5):R183-196, Sep. 20, 2011.
GenBank Accession No. AH002607.1, "Human androgen receptor gene," Oct. 31, 1994, 8 pages.
GenBank Accession No. AH002607.2, "*Homo sapiens* androgen receptor (AR) gene, complete cds," Aug. 1, 2016, 5 pages.
GenBank Accession No. FJ235916.1, "*Homo sapiens* androgen receptor splice variant 3 (AR) mRNA, complete cds, alternatively spliced," May 27, 2015, 2 pages.
GenBank Accession No. FJ235917.1, "*Homo sapiens* androgen receptor splice variant 4 (AR) mRNA, complete cds, alternatively spliced," Mar. 3, 2009, 2 pages.
GenBank Accession No. FJ235918.1, "*Homo sapiens* androgen receptor splice variant 4b (AR) mRNA, complete cds, alternatively spliced," Mar. 3, 2009, 2 pages.
GenBank Accession No. FJ235919.1, "*Homo sapiens* androgen receptor splice variant 5 (AR) mRNA, complete cds, alternatively spliced," Mar. 3, 2009, 2 pages.
GenBank Accession No. FJ235920.1, "*Homo sapiens* androgen receptor splice variant 6 (AR) mRNA, complete cds, alternatively spliced," Mar. 3, 2009, 2 pages.
GenBank Accession No. GU208210.1, "*Homo sapiens* androgen receptor variant 5,6,7es (AR) mRNA, complete cds, alternatively spliced," Dec. 14, 2009, 2 pages.
GenBank Accession No. HM055487.1, "*Homo sapiens* androgen receptor isoform 8 (AR8) mRNA, complete cds, alternatively spliced," Oct. 17, 2011, 2 pages.
GenBank Accession No. NM_ 000044.3, "*Homo sapiens* androgen receptor (AR), transcript variant 1, mRNA," May 21, 2015, 12 pages.
Guo et al., "A Novel Androgen Receptor Splice Variant Is Up-regulated during Prostate Cancer Progression and Promotes Androgen Depletion—Resistant Growth," *Cancer Res.*, 69(6):2305-2313, Mar. 2009.
Henzler et al., "Truncation and constitutive activation of the androgen receptor by diverse genomic rearrangements in prostate cancer," *Nature Communications.*, 7:13668, 2016.
Juliano., "The delivery of therapeutic oligonucleotides," *Nucleic Acids Res.*, 2016, 31 pages.
Kim et al., "TopHat-Fusion: an algorithm for discovery of novel fusion transcripts," *Genome Biol.*, 12(8):R72, 2011, 15 pages.

(Continued)

*Primary Examiner* — Amy H Bowman
(74) *Attorney, Agent, or Firm* — Fish & Richardson P.C.

(57) ABSTRACT

This document relates to materials and methods for treating cancer (e.g., prostate cancer). For example, methods for using one or more androgen receptor variant (AR-V) inhibitors (e.g., morpholinos) to treat a mammal having prostate cancer (e.g., castration-resistant prostate cancer) are provided.

25 Claims, 27 Drawing Sheets
Specification includes a Sequence Listing.

(56) References Cited

OTHER PUBLICATIONS

Knudsen et al., "Starving the Addiction: New Opportunities for Durable Suppression of AR Signaling in Prostate Cancer," *Clin Cancer Res.*, 15(15):4792-4798, Aug. 2009.

Li et al., "Androgen Receptor Splice Variants Mediate Enzalutamide Resistance in Castration-Resistant Prostate Cancer Cell Lines," *Cancer Res.*, 73(2):483-489, Jan. 2013.

Li et al., "AR intragenic deletions linked to androgen receptor splice variant expression and activity in models of prostate cancer progression," *Oncogene.*, 31:4759-4767, 2012.

Li et al., "Intragenic Rearrangement and Altered RNA Splicing of the Androgen Receptor in a Cell-Based Model of Prostate Cancer Progression," *Cancer Res.*, 71(6):2108-2117, 2011.

Lu et al., "Decoding the androgen receptor splice variants," *Transl Androl Urol.*, 2(3):178-186, Sep. 2013.

Nyquist et al., "TALEN-engineered AR gene rearrangements reveal endocrine uncoupling of androgen receptor in prostate cancer," *PNAS.*, 110(43):17492-17497, 2013.

Robinson et al., "Integrative clinical genomics of advanced prostate cancer," *Cell.*, 161(5):1215-1228, May 21, 2015.

Robinson et al., "Integrative genomics viewer," *Nat Biotechnol.*, 29(1):24-26, Jan. 2011.

Ryan et al., "Abiraterone in metastatic prostate cancer without previous chemotherapy," *N Engl J Med.*, 368(2):138-148, Jan. 10, 2013.

Ryan et al., "Evidence that polyadenylation factor CPSF-73 is the mRNA 3' processing endonuclease," *RNA.*, 10(4):565-573, Apr. 2004.

Schonemann et al., "Reconstitution of CPSF active in polyadenylation: recognition of the polyadenylation signal by WDR33," *Genes Dev.*, 28:2381-2393, 2014.

Shi et al., "Molecular architecture of the human pre-mRNA 3' processing complex," *Mol Cell.*, 33(3):365-376, Feb. 13, 2009.

Sridharan and Gogtay, "Therapeutic nucleic acids: current clinical status," *Br J Clin Pharmacol.*, 82:659-672, 2016.

Summerton., "Morpholino, siRNA, and S-DNA Compared: Impact of Structure and Mechanism of Action on Off-Target Effects and Sequence Specificity," *Curr Topics Med Chem.*, 7:651-660, 2007.

The Cancer Genome Atlas Research Network., "The Molecular Taxonomy of Primary Prostate Cancer," *Cell.*, 163(4):1011-1025, Nov. 5, 2015.

Torre et al., "Global cancer statistics, 2012," *CA Cancer J Clin.*, 65(2):87-108, Mar. 2015.

Uphoff et al., "Treatment of Mycoplasma Contamination in Cell Cultures with Plasmocin," *J Biomed Biotechnol.*, 2012:267678, 2012, 8 pages.

Van Etten et al., "Human Pumilio Proteins Recruit Multiple Deadenylases to Efficiently Repress," *J Biol Chem.*, 287:36370-36383, 2012.

Wu et al., "ROAST: rotation gene set tests for complex microarray experiments," *Bioinformatics.*, 26(17):2176-2182, Sep. 1, 2010.

Yu et al., "Rapid Induction of Androgen Receptor Splice Variants by Androgen Deprivation in Prostate Cancer," *Clin Cancer Res.*, 20(6):1590-1600, Mar. 2014.

\* cited by examiner

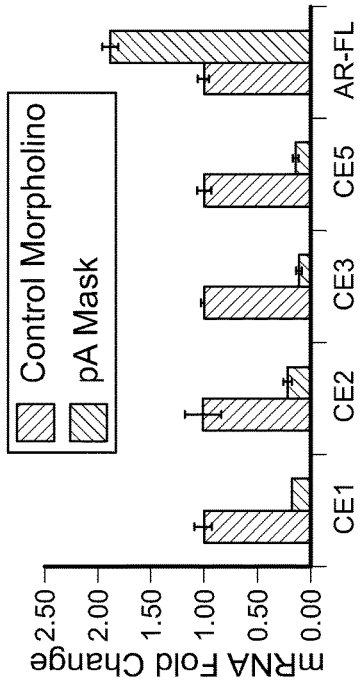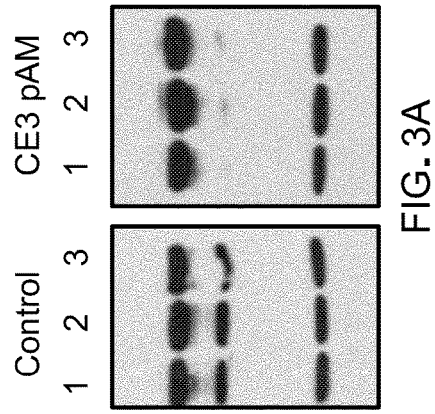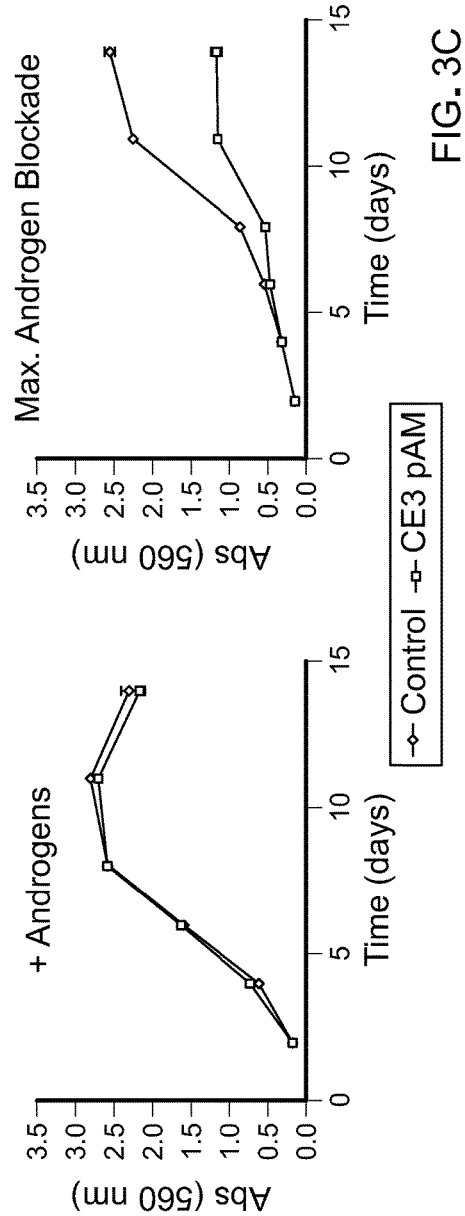
FIG. 3A
FIG. 3B
FIG. 3C

3'
Undup3: TATATAACAATTTCAGAGAGTCCAC GGACTCTCTGAAATTGTTATAAGGT
Undup2: ATAACAATTTCAGAGAGTCCACATA TTGTTATAAGGTCTTTTTCTTTGTT
Undup1: TATATAACAATTTCAGAGAGTCCAC GGACTCTCTGAAATTGTTATAAGGT

SSA
TALEN
AR

5'
Undup3: ATGAACATTCCTGCCTGGCTGACAT CTTTACTCATATATACTTTAGATTC
Undup2: GGATGAACATTCCTGCCTGGCTGAC GGTGGCGGCAAGCAAGCGCTCGAAA
Undup1: ATGAACATTCCTGCCTGGCTGACAT CTTTACTCATATATACTTTAGATTC

FIG. 7

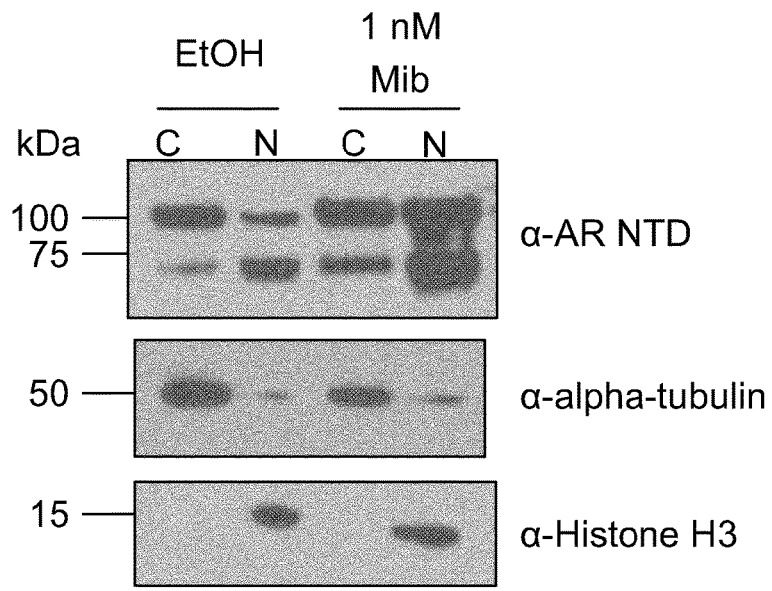

FIG. 8

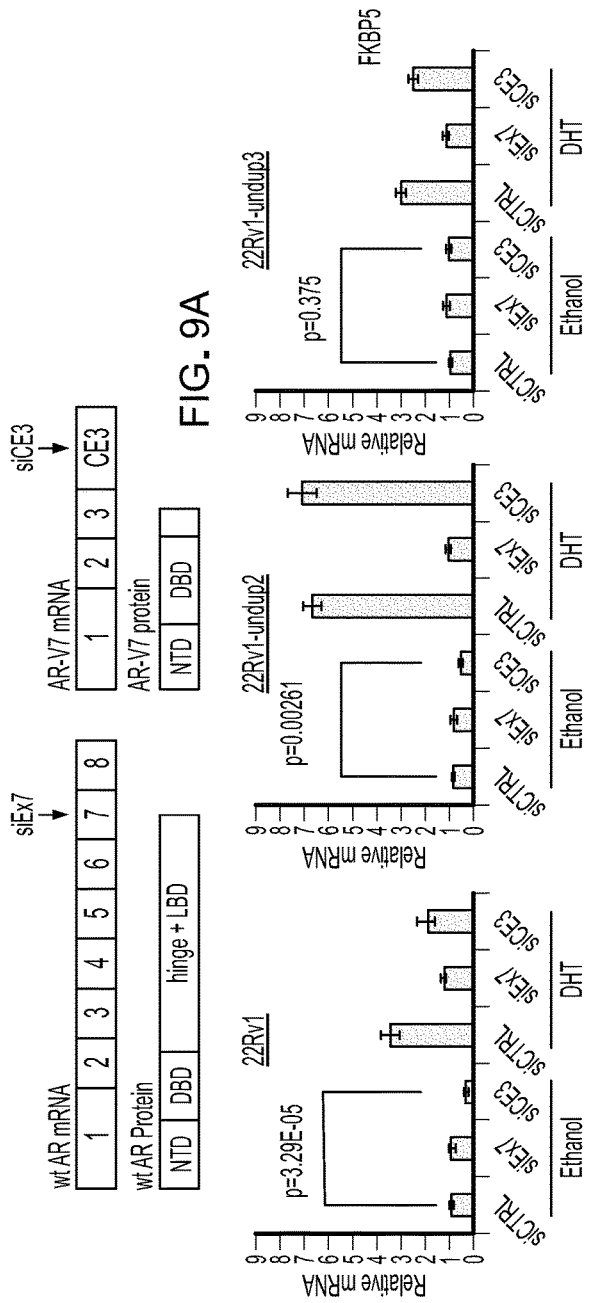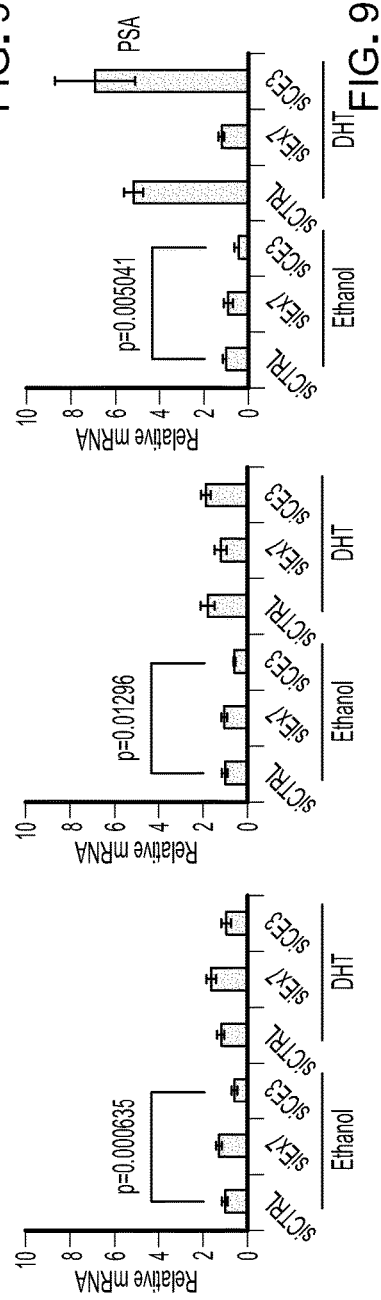
FIG. 9A
FIG. 9B
FIG. 9C

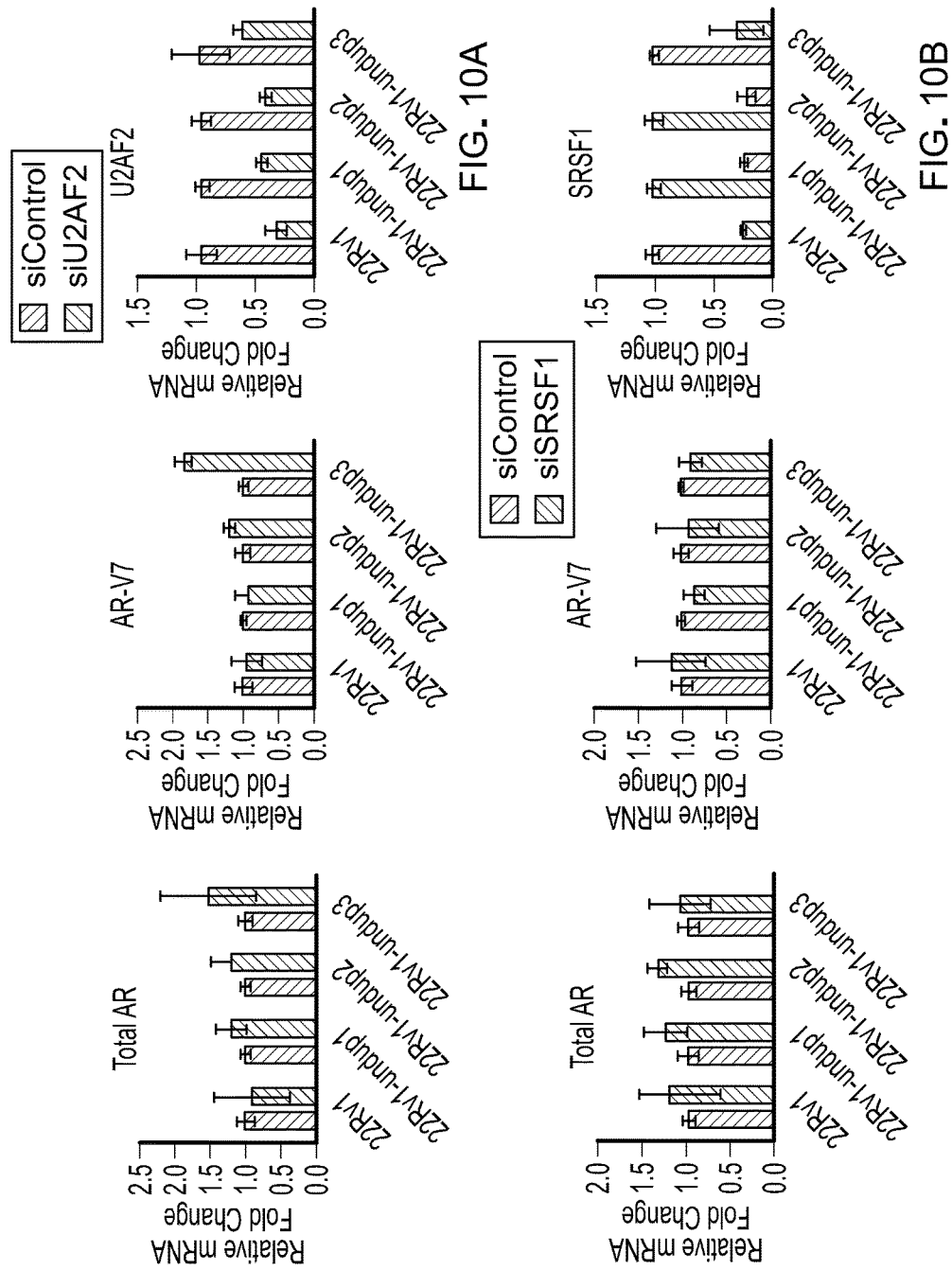

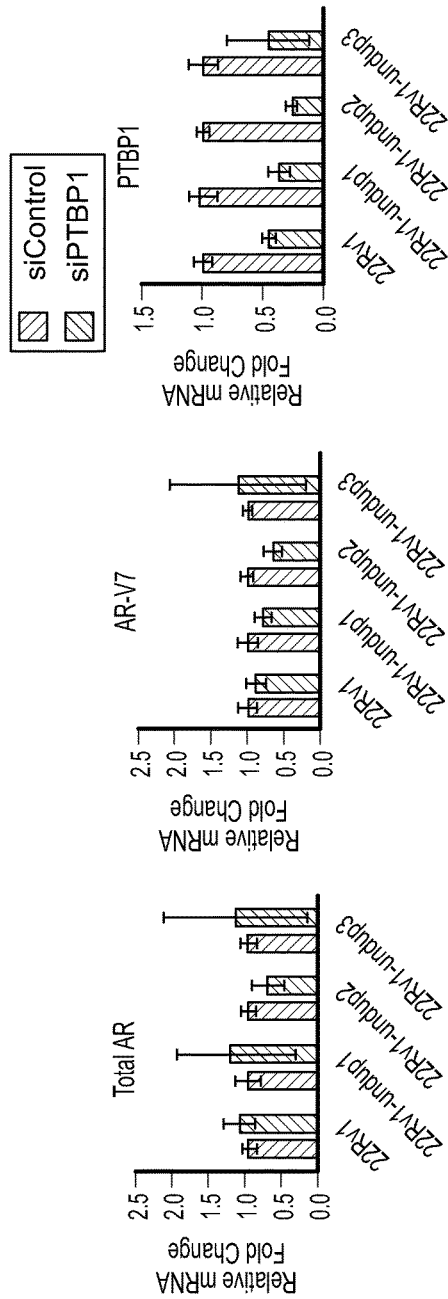
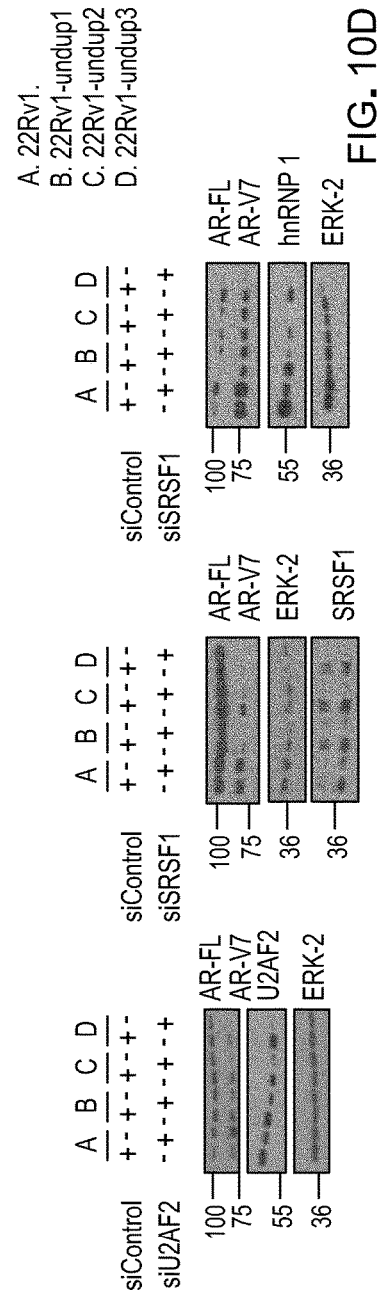
FIG. 10C
FIG. 10D

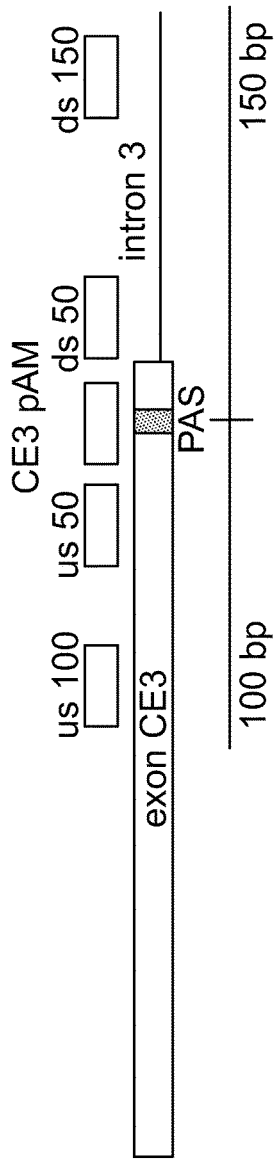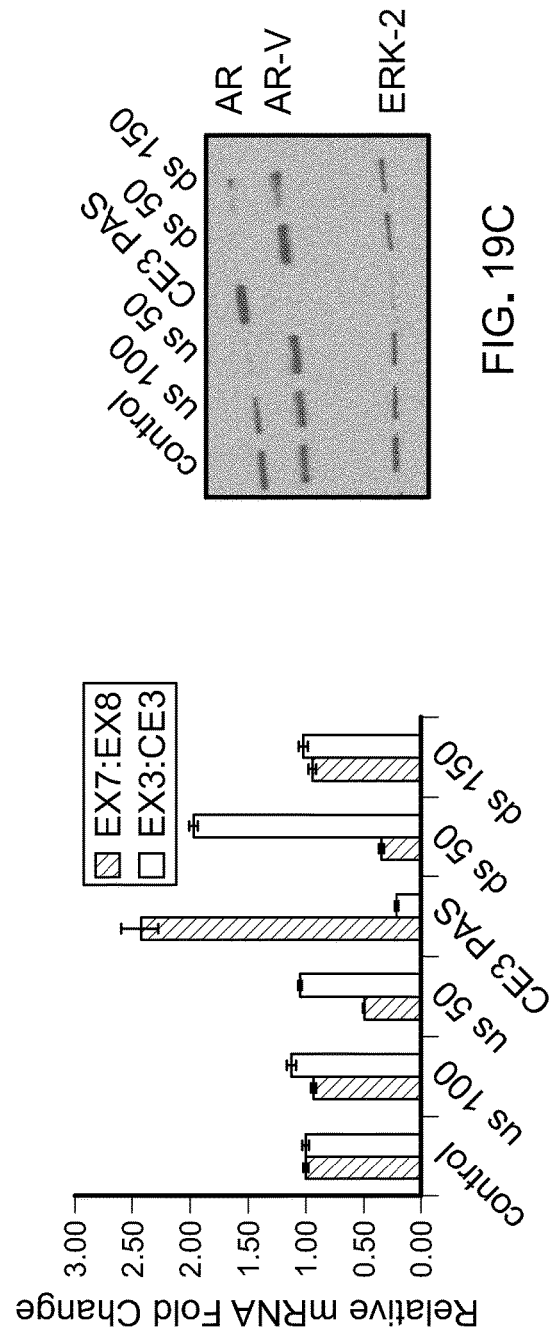
FIG. 19A
FIG. 19B
FIG. 19C

ANDROGEN RECEPTOR VARIANT INHIBITORS AND METHODS OF USING

CROSS-REFERENCE TO RELATED APPLICATIONS

This application claims the benefit of U.S. Patent Application Ser. No. 62/374,482, filed on Aug. 12, 2016. The disclosure of the prior application is considered part of (and is incorporated by reference in) the disclosure of this application.

FEDERAL FUNDING

This invention was made with government support under CA174777 and T32-CA009138 awarded by the National Institutes of Health. The government has certain rights in the invention.

BACKGROUND

1. Technical Field

This document relates to materials and methods for treating cancer (e.g., prostate cancer). For example, this document provides methods for using one or more androgen receptor variant (AR-V) inhibitors (e.g., morpholinos) to treat a mammal having prostate cancer (e.g., castration-resistant prostate cancer).

2. Background Information

Prostate cancer (PCa) is the most frequently diagnosed cancer in males and accounts for an estimated 142,000 deaths in developed countries each year (Torre et al., 2015 *CA Cancer J Clin* 65:87-108). In normal prostate cells, the androgen receptor (AR) functions as a master transcriptional regulator activated by the androgens, testosterone and dihydrotestosterone; accordingly, PCa presents as an androgen and androgen receptor (AR)-dependent disease (Dehm et al., 2011 *Endocr Relat Cancer* 18:R183-96). For many, surgery and radiation are curative. However, a significant number of patients are diagnosed with metastatic disease, or experience recurrence after first line interventions. The standard systemic treatment for these men is androgen deprivation therapy (ADT), which includes surgical castration, pharmacologic castration, and antiandrogens to suppress AR transcriptional activity (Dehm et al., 2011 *Endocr Relat Cancer* 18:R183-96). However, development of resistance and transition to castration-resistant prostate cancer (CRPC) is a major clinical challenge characterized by rising PSA levels (signifying reactivation of AR transcriptional activity), an increase in tumor size, and metastatic spread (Knudsen et al., 2009 *Clin Cancer Res* 15:4792-8). Second-line ADT drugs that provide a more effective blockade of androgen synthesis (abiraterone), or serve as a higher-affinity AR antagonists (enzalutamide) have recently been approved to treat CRPC (Ryan et al., 2013 *N Engl J Med* 368:138-48; Beer et al., 2014 *N Engl J Med* 371:424-33). However, improvements in overall survival still are measured in months and CRPC remains uniformly lethal.

SUMMARY

This document provides materials and methods for treating cancer (e.g., prostate cancer). For example, this document provides methods for using one or more AR-V inhibitors (e.g., morpholinos) to treat a mammal having prostate cancer (e.g., CRPC, also commonly referred to as androgen-independent PCa).

All AR-targeted therapies require that the patient have an AR with an intact ligand binding domain (LBD) (Li et al., 2013 *Cancer Res* 73:483-9). Normal AR is polyadenylated via a canonical polyadenylation signal (PAS) in exon 8. AR variants (AR-Vs) arise from splicing of cryptic exons (CEs) downstream of AR exon 3 (CE3), or skipping of exons encoding the AR LBD (Dehm et al., 2011 *Endocr Relat Cancer* 18:R183-96). In CRPC, expression of AR-Vs lacking a LBD results in constitutively active transcription factors that drive androgen-independent growth of prostate cancer cells and escape from AR-targeted therapies.

As described herein, a morpholino that targets a non-canonical PAS in CE3 can be administered to CRPC cells to inhibit non-canonical splicing and reduce mRNA and/or protein levels of one or more AR-Vs. A morpholino targeting a PAS in CE3 can also redirect splicing of full length AR to restore androgen responsiveness to a CRPC.

In general, one aspect of this document features an AR-V inhibitor oligonucleotide that includes an antisense sequence which is complementary to a target sequence in an AR transcript and includes at least one modified nucleotide. The AR-V inhibitor oligonucleotide can bind to the AR transcript and can inhibit expression of one or more AR-Vs. The antisense sequence can be about 5 nucleotides to about 200 nucleotides (e.g., about 22 to about 30 nucleotides) in length. In some aspects, the antisense sequence is 25 nucleotides in length. The antisense sequence can include the sequence TTTATT (SEQ ID NO:1). The antisense sequence can include the sequence GTGTATTAATGGCTTTAT-TAAGGGA (SEQ ID NO:2). The target sequence in the AR transcript can modulate AR-V splicing. The target sequence can be in intron 3. The target sequence can be in cryptic exon 3. The target sequence can be a polyadenylation site. The target sequence can include the sequence AAUAAA (SEQ ID NO:3). The target sequence can include the sequence UCCCUUAAUAAAGCCAUUAAUACAC (SEQ ID NO:4). The AR-V inhibitor oligonucleotide can inhibit expression of one or more AR-Vs that lack an androgen receptor ligand binding domain (e.g., AR-V2, AR-V5, AR-V7, and/or AR-V9). The AR-V inhibitor oligonucleotide can inhibit expression of AR-V7. The AR-V inhibitor oligonucleotide can be conjugated to a cell-penetrating peptide (e.g., an 8 guanidine head group). The at least one modified nucleotide can include a morpholine ring. The at least one modified nucleotide can include a phosphorodiamidate linkage. The AR-V inhibitor oligonucleotide can be a morpholino.

In another aspect, this document features a method for treating CRPC in a mammal. The method includes, or consists essentially of, administering to the mammal an AR-V inhibitor oligonucleotide, where the AR-V inhibitor oligonucleotide includes an antisense sequence which is complementary to a target sequence in an AR transcript. In some aspects, a method for treating CRPC in a mammal can also include identifying the mammal as having a CRPC expressing one or more AR-Vs. In some aspects, a method for treating CRPC in a mammal can also include determining that an AR-V is expressed in the CRPC. The mammal can be a human. The AR-V inhibitor oligonucleotide can inhibit expression of one or more AR-Vs. The AR-V inhibitor oligonucleotide can inhibit expression of one or more AR-Vs that lack an androgen receptor ligand binding domain (e.g., AR-V2, AR-V5, AR-V7, and/or AR-V9). The AR-V inhibitor oligonucleotide can inhibit expression of AR-V7. The AR-V inhibitor oligonucleotide can restore androgen responsiveness to a CRPC. The antisense sequence can be about 22 to about 30 nucleotides (e.g., 25 nucleotides) in length. The antisense sequence can include the sequence TTTATT (SEQ ID NO:1). The antisense sequence can include the sequence GTGTATTAATGGCTT-TATTAAGGGA (SEQ ID NO:2). The target sequence in the AR transcript can modulate AR-V splicing. The target sequence can be a polyadenylation site. The target sequence can include the sequence AAUAAA (SEQ ID NO:3). The target sequence can include the sequence UCCCUUAAUAAAGCCAUUAAUACAC (SEQ ID NO:4). The at least one modified nucleotide can include a morpholine ring. The at least one modified nucleotide can include a phosphorodiamidate linkage. The AR-V inhibitor oligonucleotide can be a morpholino. A method for treating CRPC in a mammal can also include administering to the mammal an additional cancer treatment. The additional cancer treatment can include androgen deprivation therapy. The androgen deprivation therapy can include administering an antiandrogen (e.g., enzalutamide).

In another aspect, this document features a method for modulating AR splicing. The method includes, or consists essentially of, administering to a mammal an AR-V inhibitor oligonucleotide, where the AR-V inhibitor oligonucleotide includes an antisense sequence which is complementary to a target sequence in an AR transcript, and where the AR-V inhibitor oligonucleotide can bind to the AR transcript and modulate AR splicing. The AR-V inhibitor oligonucleotide can inhibit non-canonical splicing of the AR transcript to express an AR-V. The AR-V inhibitor oligonucleotide can inhibit expression of one or more AR-Vs that lack an androgen receptor ligand binding domain (e.g., AR-V2, AR-V5, AR-V7, and/or AR-V9). The AR-V inhibitor oligonucleotide can inhibit expression of AR-V7. The AR-V inhibitor oligonucleotide can direct splicing of the AR transcript to express a full length AR. The antisense sequence can be about 22 to about 30 nucleotides (e.g., 25 nucleotides) in length. The antisense sequence can include the sequence TTTATT (SEQ ID NO:1). The antisense sequence can include the sequence GTGTATTAATGGCTT-TATTAAGGGA (SEQ ID NO:2). The target sequence can include the sequence AAUAAA (SEQ ID NO:3). The target sequence can include the sequence UCCCUUAAUAAAGCCAUUAAUACAC (SEQ ID NO:4). The at least one modified nucleotide can include a morpholine ring. The at least one modified nucleotide can include a phosphorodiamidate linkage. The AR-V inhibitor oligonucleotide can be a morpholino.

In another aspect, this document features a pharmaceutical composition including an AR-V inhibitor oligonucleotide, where the AR-V inhibitor oligonucleotide includes an antisense sequence which is complementary to a target sequence in an AR transcript and at least one modified nucleotide, where the AR-V inhibitor oligonucleotide can bind to the AR transcript and can inhibit expression of one or more AR-Vs.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A shows the structure of an exemplary morpholino backbone sequence. Morpholinos are characterized by the phosphorodiamidate linkage and morpholine ring. FIG. 2B shows the target site of an exemplary morpholino, termed CE3 pAM (SEQ ID NO:2), targeting a sequence of AR mRNA (SEQ ID NO:4) containing the PAS in CE3 (SEQ ID NO:3).

FIGS. 3A-3C show that a morpholino targeting the PAS in CE3 inhibits AR-V expression and restores androgen responsiveness to CRPC cells. FIGS. 3A and 3B show that CE3 pAM transfection blocks AR-V protein (A) expression and AR-V2, AR-V5, AR-V7, and AR-V9 mRNA expression (B) in E43 cells. FIG. 3C shows crystal violet staining that indicates that transfection of CE3 pAM blocks growth of E43 cells cultured under maximal androgen blockade.

FIG. 5A contains a drawing of a TALEN engineering strategy where tAR-2 TALENs were designed to cut AR (arrows) and delete the 22Rv1 duplication. FIG. 5B contains a schematic of the use of an mCherry/split GFP reporter harboring a tAR-2 cut site (CS; arrow) to identify, sort, and plate transfected cells with tAR-2 activity. FIG. 5C contains western blots of cells cultured in steroid-deplete medium and treated with 1 nM dihydrotestosterone (DHT), 10 μM enzalutamide (Enza), or vehicle control as indicated. Blots were probed with antibodies specific for AR (N20), AR-V7, or ERK2 (loading control). FIG. 5D contains graphs and western blots showing growth of cells transfected with indicated siRNAs was assessed by crystal violet staining. Bars represent mean fold growth on Day 6 relative to Day 0 (n=12, error bars=95% confidence intervals). **p≤0.0001, p≤0.01, ns p>0.05, Mann Whitney U tests. Bottom panels illustrate western blots of lysates from transfected cells, probed with antibodies as in C.

FIG. 6A contains an image of a PCR digest assay confirming tAR-2 activity. The PCR digest assay measured nonhomologous end joining (NHEJ) mutations induced within the cleavage site in the spacer sequence between TALEN binding sites. An AflIII endonuclease site located in the spacer sequence; thus, error prone NHEJ from tAR-2 induced dsDNA breaks, induced mutations in the AflIII site, rendering the site resistant to AflIII digestion. FIG. 6B contains a diagram of multiplex ligation-dependent probe amplification (MLPA) of 22Rv1 and undup1-3 sub-lines. Probes were designed to target AR exons 1-8, and introns at the specified genomic locations (top panel).

FIG. 7 is a diagram of breakpoint sequence junctions of 22Rv1 sub-lines. The 3' undup3 (SEQ ID NO:5), 3' undup2 (SEQ ID NO:6), 3' undup1 (SEQ ID NO:7), 5' undup3 (SEQ ID NO:8), 5' undup2 (SEQ ID NO:9), and 5' undup1 (SEQ ID NO:10) breakpoint sequence junctions are shown. Different colors represent sequence origin; SSA reporter sequence (black), TALEN (highlighted), AR gene (gray).

FIG. 8 contains a western blot showing that AR localizes to the nucleus upon stimulation with 1 nM mibolerone in 22Rv1-undup3 cells. AR variants are constitutively nuclear. Cells were cultured under androgen-free conditions for 24 hours and then treated for 24 hours with medium containing 1 nM mibolerone (Mib, synthetic androgen) or ethanol (EtOH, vehicle control). Cell lysates were fractionated into cytoplasmic (C) or nuclear (N) fractions and analyzed by Western blot with AR-NTD, alpha-tubulin (cytoplasmic marker), and Histone-H3 (nuclear marker)-specific antibodies.

FIGS. 9A-9E show an AR target gene expression panel. FIG. 9A contains schematics showing siRNAs targeting exon 7 to knock down FL-AR and siRNAs targeting CE3 to knock down AR-V7. FIGS. 9B-9E contains graphs showing relative mRNA levels of AR target genes FKBPS (B), PSA (C), TMPRSS2 (D), and hK2 (E) as assessed by RT-qPCR. Error bars represent the standard error of the mean (n=8). Significance was determined using a two-tailed t-test. GAPDH was used as an internal control.

FIGS. 10A-10D show that knockdown of splicing factors U2AF2, SRSF1, and PTBP1. FIGS. 10A-10C contains graphs of RT-qPCR experiments showing the effect of splicing factor knockdown on levels of total AR and AR-V7 mRNA relative to nontargeting controls (n=4). GAPDH was used as an internal control (calibrator) for RT-qPCR experiments. Error bars represent 95% confidence intervals. FIG. 10D contains a western blot showing the effect of splicing factor knockdown on levels of total AR and AR-V7 protein relative to nontargeting controls.

FIG. 11A contains a schematic of predicted AR RNA-seq coverage based on use of annotated splice junctions and PASs in AR cryptic exons (CEs). FIG. 11B contains a proposed single PAS model based on the observed AR RNA-seq coverage from 22Rv1 and metastatic biopsies (top) that are consistent with multiple AR-Vs arising from use of multiple splice acceptor sites that terminate at a single PAS (bottom). The location at which CE3 pAM morpholino binds to induce steric blockade is shown. FIG. 11C contains graphs showing relative mRNA levels and western blots showing relative protein levels. Left panels: 22Rv1-undup3 (top) and 22Rv1 (bottom) cells were transfected with 10 μM control or CE3-pAM. Mean mRNA fold change of AR and AR-Vs relative to actin control is shown (n=6, error bars=95% confidence intervals). **p≤0.0001, unpaired t-tests. Right panels: western blot of lysates from transfected cells, probed with antibodies to AR NTD or ERK-2 (loading control). FIG. 11D contains graphs of crystal violet staining to assess growth of 22Rv1-undup3 (left) and 22Rv1 (right) cells transfected as in panel C maintained in androgen-deplete medium (CSS) in the presence of 1 nM DHT or vehicle control (ethanol). Data points represent means (n=6, 22Rv1-undup1, n=4, 22Rv1; error bars=95% confidence intervals). p≤0.0001, p≤0.01, ns p>0.05 p-values in a two-tailed t-test.

FIG. 14A contains a ROAST enrichment analysis of a set of 91 genes involved in mRNA 3' end processing in 52 tumor/matched normal TCGA RNA-seq samples. FIG. 14B contains oncoprints depicting CPSF core complex gene alterations in primary and metastatic prostate cancer. FIG. 14C contains graphs showing AR and AR-V mRNA levels in 22Rv1-undup3 cells transfected with siRNAs targeting CPSF core complex genes, relative to 18S internal control. Bars represent means (n=6, error bars=95% confidence intervals. **p≤0.0001, p≤0.01, ns p>0.05, unpaired t-test. FIG. 14D contains a heatmap of $\log_2$ fold changes in mRNA expression of CPSF core complex factors in primary prostate cancer compared to normal tissue (52 matched samples).

FIG. 18A contains a western blot with lysates from 22Rv1-undup3 transfected with four independent and pooled siRNAs. Blots were probed with antibodies to CPSF1 or ERK-2 (loading control). FIG. 18B contains a western blot with lysates from 22Rv1-undup3 cells transfected with CPSFS1 siRNA as in panel A, probed with antibodies to AR, ERK-2 (loading control), or AR-V7. FIG. 18C contains a graph of growth of 22Rv1-undup3 cells transfected as with CPSF1. siRNA was assessed under androgen replete (charcoal stripped serum+1 nM DHT) or androgen deplete (charcoal-stripped serum+ethanol, vehicle control) conditions by crystal violet staining. Data points represent means (n=6, error bars=95% confidence intervals). ****p≤0.0001, *p≤0.05, ns p>0.05, unpaired t-test. FIG.

18D contains a model for AR splicing decisions regulated by CPSF1-dependent selection of a single PAS in AR intron 3.

FIGS. 19A-19C specificity of CE3 pAM for the PAS in AR CE3. FIG. 19A contains a schematic of morpholinos designed to bind regions upstream and downstream of the PAS in CE3. FIG. 19B is a graph showing mean relative fold change of AR and AR-V7 mRNA relative to actin control 24 hours after transfection of 10 µM indicated morpholino. Data points represent means from one biological replicate and three technical replicates (n=3; error bars indicate standard deviation from the mean). FIG. 19C is an image of a Western blot of lysates from transfected cells, probed with antibodies to AR N terminal domain or ERK-2 (loading control).

Figure 20:
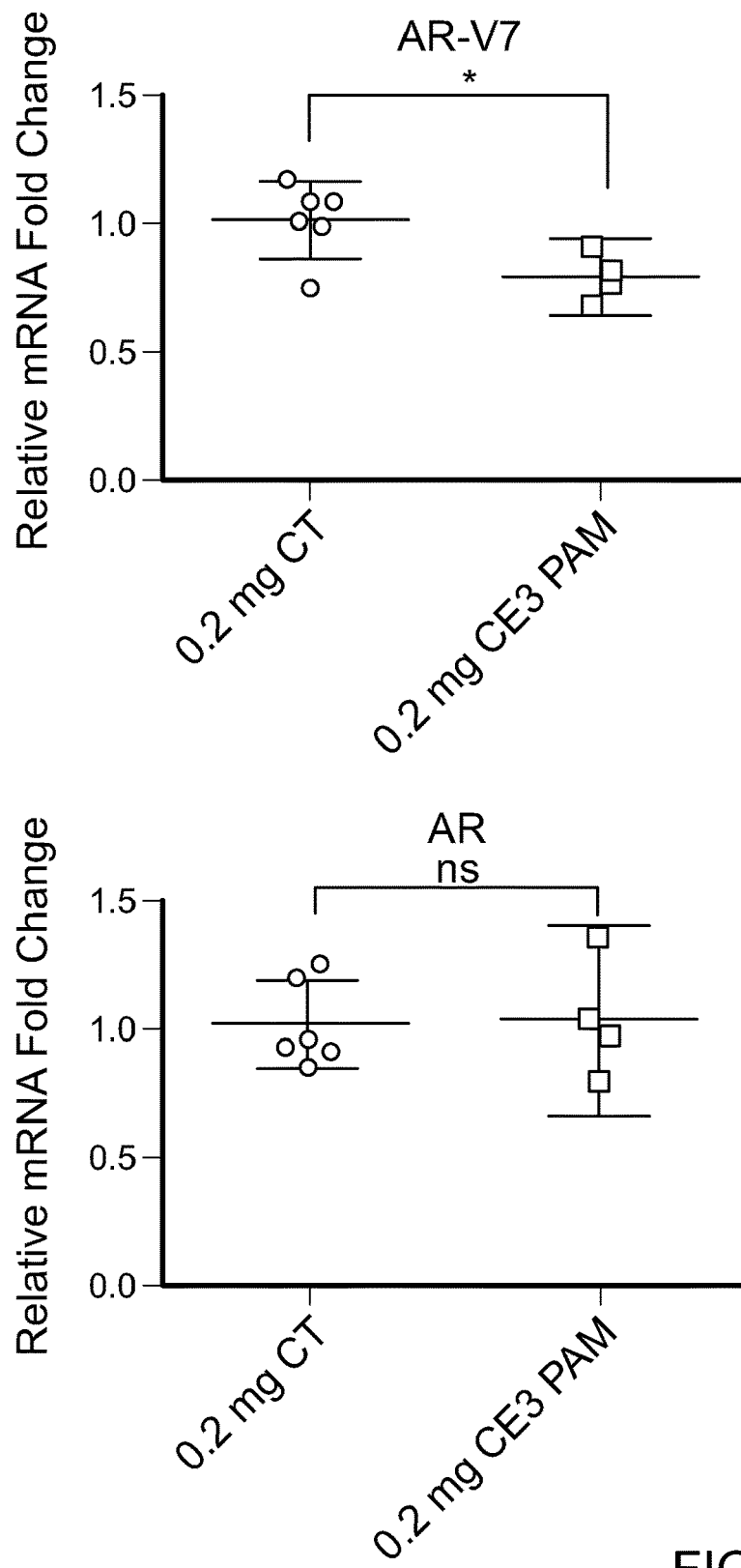

FIG. 20 shows the impact of intratumoral CE3 pAM on AR and AR-V mRNA levels. Mean relative fold change of AR (right) and AR-V7 (left) mRNA relative to actin control 24 hours after final of three intratumoral injections of 0.2 mg control or CE3 pAM vivo-morpholino. Data points represent means (n=4, CE3 pAM group, n=6, control group; error bars=95% confidence intervals). *p≤0.05 in a two-tailed t-test.

DETAILED DESCRIPTION

This document provides materials and methods for treating cancer (e.g., prostate cancer). In some cases, this document provides methods for using one or more AR-V inhibitors (e.g., AR-V inhibitor oligonucleotides such as morpholinos) to treat a mammal having prostate cancer (e.g., CRPC). In some cases, an AR-V inhibitor provided herein can be a morpholino that targets a non-canonical PAS in a CE (e.g., CE3) and inhibits non-canonical splicing to reduce mRNA and/or protein levels of one or more AR-Vs. For example, a morpholino provided herein can be used to reduce AR-V polypeptide expression. For example, a morpholino provided herein can be used to direct splicing to express full length AR. For example, a morpholino provided herein can be used to restore androgen responsiveness to a CRPC.

Provided herein are AR-V inhibitors (e.g., AR-V inhibitor oligonucleotides) that can reduce and/or inhibit AR-V polypeptide expression or AR-V polypeptide activity. Oligonucleotides that reduce and/or inhibit AR-V polypeptide expression can, for example, reduce and/or eliminate splicing of AR mRNA into AR-Vs. Examples of oligonucleotides that reduce and/or inhibit AR-V polypeptide expression include, without limitation, antisense oligonucleotides (e.g., morpholinos), nucleic acid molecules designed to induce RNA interference (e.g., a siRNA molecule or a shRNA molecule), micro RNAs (miRNAs), aptamers, RNA decoys, and circular RNAs (see, e.g., Sridharan and Gogtay 2016 *Br J Clin Pharmacol* 82:659-672). In some cases, an AR-V inhibitor provided herein can be a morpholino that inhibits expression of one or more AR-Vs.

An AR-V inhibitor (e.g., an AR-V inhibitor oligonucleotide) provided herein can be complementary to (e.g., include an antisense sequence) an AR transcript (e.g., pre-mRNA) such that the AR-V inhibitor can target (e.g., bind to) the AR transcript can inhibit expression of one or more AR-Vs. An AR-V inhibitor oligonucleotide provided herein can include a nucleic acid sequence that is about 5 nucleotides to about 200 nucleotides in length (e.g., about 8 to about 150, about 10 to about 100, about 12 to about 75, about 15 to about 50, or about 22 to about 30 nucleotides in length). In some cases, an AR-V inhibitor oligonucleotide provided herein can include a nucleic acid sequence that is about 22 to about 30 nucleotides in length. For example, an AR-V inhibitor oligonucleotide provided herein can be about 25 nucleotides in length.

An AR-V inhibitor (e.g., an AR-V inhibitor oligonucleotide) provided herein can inhibit expression of one or more AR-Vs (e.g., AR-V1, AR-V2, AR-V3, AR-V4, AR-V5, AR-V6, AR-V7, AR-V8, AR-V9, AR-V10, AR-V11, AR-V12, AR-V13, AR-V14, AR-V15, AR-V16, or AR-V18). An AR-V inhibitor provided herein can inhibit expression of one or more AR-Vs lacking the AR LBD. For example, an AR-V inhibitor provided herein can inhibit expression of one or more of AR-V7, AR-V2, AR-V5, and/or AR-V9. An AR-V inhibitor provided herein can target AR and inhibit expression of AR-V7.

An AR-V inhibitor (e.g., an AR-V inhibitor oligonucleotide) provided herein can be complementary to (e.g., can include an antisense sequence targeting) a nucleic acid sequence within an AR transcript (e.g., pre-mRNA) that modulates AR-V splicing. For example, an AR-V inhibitor provided herein can be include an antisense sequence that is complementary to a nucleic acid sequence within an AR pre-mRNA that directs splicing of exon 3 to a CE within intron 3 (e.g., CE1, CE2, CE5, or CE3). An AR-V inhibitor provided herein can include an antisense sequence that is complementary to a PAS in CE3. In some cases, an antisense sequence that is complementary to a PAS in CE3 can include the sequence: TTTATT (SEQ ID NO:1). For example, an antisense sequence that is complementary to a PAS in CE3 can include the sequence: GTGTATTAATGGCTTTAT-TAAGGGA (SEQ ID NO:2). An AR-V inhibitor oligonucleotide provided herein can be have at least 75 percent sequence identity (e.g., at least 80%, at least 82%, at least 85%, at least 88%, at least 90%, at least 93%, at least 95%, at least 97% or at least 99% sequence identity) to SEQ ID NO:2, provided it binds to an AR transcript and inhibits expression of one or more AR-Vs.

Figure 1:
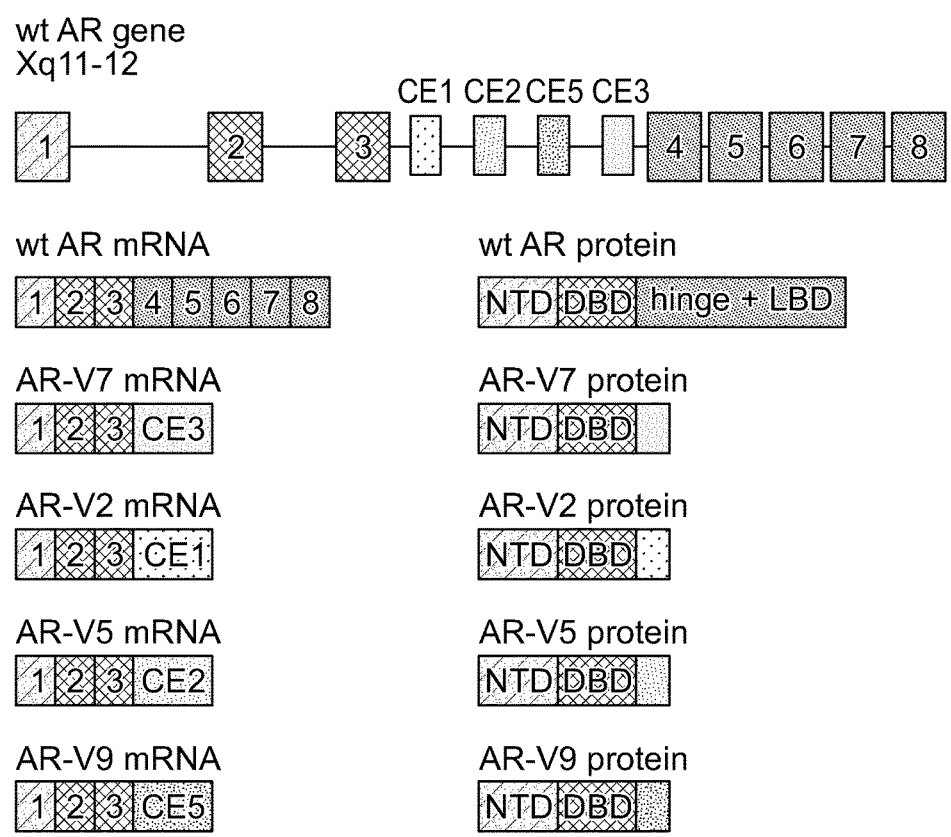
FIG. 1 shows that the wild type (wt) AR gene encodes 8 exons, labeled 1-8. Exon 1 encodes the NTD (blue). Exons 2-3 encode the DBD (green). Exons 4-8 encode the LBD (orange). Cryptic exons (CEs) lie in intron 3, and are labeled CE1, CE2, CE5, and CE3 (purple). AR-V7 mRNA lacks exons 4-8 and, instead, harbors a terminal exon CE3. AR-V2 harbors terminal exon CE1. AR-V5 harbors terminal exon CE2. AR-V9 harbors terminal exon CE5.

An AR-V inhibitor (e.g., an AR-V inhibitor oligonucleotide) provided herein can target (e.g., bind to) any appropriate sequence within an AR transcript (e.g., pre-mRNA). Schematic representations of AR transcripts and AR-Vs are shown in FIG. 1. Appropriate target sequences within AR include, for example, sequences that modulate splicing of AR mRNA into AR-Vs (e.g., sequences within AR intron 3). An AR-V inhibitor provided herein can target a sequence within a CE in AR intron 3 (e.g., CE1, CE2, CE5, or CE3). For example, an AR-V inhibitor provided herein can target CE3 in AR intron 3. An AR-V inhibitor provided herein can target a PAS (e.g., a consensus PAS) in intron 3. For example, an AR-V inhibitor provided herein can target a consensus PAS in CE3 in AR intron 3. An AR-V inhibitor provided herein can target a sequence within an AR transcript that is about 4 nucleotides to about 250 nucleotides in length (e.g., about 4 to about 200, about 5 to about 150, about 5 to about 85, about 6 to about 30, or about 6 to about 25 nucleotides in length) and contains a PAS. In some cases, an AR-V inhibitor target sequence can include a PAS (e.g., a consensus PAS) of human CE3 in AR intron 3: AAUAAA (SEQ ID NO:3). For example, an AR-V inhibitor target sequence can include a 25 nucleotide sequence containing the PAS of human AR CE3: UCCCUUAAUAAAGC-CAUUAAUACAC (SEQ ID NO:4).

Additional AR-V inhibitors can be readily designed based upon the nucleic acid sequences of AR-Vs. Examples of AR-V nucleic acids include, without limitation, the human AR-V sequences set forth in GenBank® Accession Nos. NM_000044 (Version NM_000044.3, GI: 349501065), AH002607 (see, e.g., Version AH002607.1, GI: 178881; and Version AH002607.2, GI: 1049010826), FJ235917 (see, e.g., Version FJ235917.1, GI: 224181615), FJ235918 (see, e.g., Version FJ235918.1, GI: 224181617), FJ235916 (see, e.g., Version FJ235916.1, GI: 224181613), FJ235919 (see, e.g., Version FJ235919.1, GI: 224181619), FJ235920 (see, e.g., Version FJ235920.1, GI: 224181621), HM055487 (see, e.g., Version HM055487.1, GI: 302028368), and GU208210 (see, e.g., Version GU208210.1, GI: 270358641).

An AR-V inhibitor (e.g., an AR-V inhibitor oligonucleotide) provided herein can include at least one modified nucleotide. Nucleotides can be modified for any appropriate purpose including, for example, increased stability, and/or detection. A modification in an oligonucleotide can be in the nucleotide (e.g., the backbone, the sugar, and the nucleobase), the linkage, or any combination thereof. Examples of modified nucleotides include, without limitation, nucleotides containing morpholine rings, peptide nucleic acids (PNAs), locked nucleic acids (LNAs), glycol nucleic acids (GNAs), threose nucleic acids (TNAs), nucleotides containing allylamine, nucleotides containing biotin, nucleotides containing fluorescein, nucleotides containing-methyl, and/or dideoxynucleotides. Examples of modified linkages include, without limitation, phosphoroamidate linkages, phosphorothioate linkages, phosphordithioate linkages, and/or phosphodiester linkages. Modified nucleotides can be as described elsewhere (see, e.g., Juliano 2016 Nucleic Acids Research doi: 10.1093/nar/gkw236). In some cases, an AR-V inhibitor oligonucleotide provided herein is a morpholino (e.g., an oligonucleotide having nucleotides containing morpholine rings and phosphorodiamidate linkages).

An AR-V inhibitor (e.g., an AR-V inhibitor oligonucleotide) provided herein also can include additional molecules to facilitate cellular uptake and/or monitoring of the AR-V inhibitor. Molecules that facilitate cellular uptake and/or monitoring can be oligonucleotide sequences or polypeptide sequences. Molecules that facilitate cellular uptake and/or monitoring can be included by any appropriate manner. For example, when a molecule that facilitates cellular uptake and/or monitoring is an oligonucleotide, an AR-V inhibitor oligonucleotide can include an oligonucleotide sequence that facilitates cellular uptake and/or monitoring of the AR-V inhibitor. For example, when a molecule that facilitates cellular uptake and/or monitoring is a polypeptide, an AR-V inhibitor oligonucleotide can be conjugated (e.g., through covalent and/or non-covalent linkages) to a polypeptide sequence that facilitates cellular uptake and/or monitoring of the AR-V inhibitor. Examples of oligonucleotide sequences that can facilitate cellular uptake of an AR-V inhibitor oligonucleotide include, for example, a nuclear localization signal (NLS). Examples of polypeptide sequences that can facilitate cellular uptake of an AR-V inhibitor include, for example, cell-penetrating peptides (CPPs; such as an 8 guanidine head group and/or 8 arginine residues (e.g., 8 D-arginine residues)), GalNAc clusters, poly(ethylene amine), cationic polymers, biodegradable polymers, poly(L) lysine, and poly(2-dimethylamino ethylamino) phosphazine). In some cases, an AR-V inhibitor provided herein includes an 8 guanidine head group. Examples of polypeptides that can facilitate monitoring (e.g., in vivo, ex vivo, and/or in vitro monitoring) of an AR-V inhibitor oligonucleotide include, for example, reporter sequences (e.g., fluorescent peptides, bioluminescent peptides, or selectable markers), epitope tags (e.g., hemagglutinin (HA), FLAG®, maltose-binding protein (MBP), cellulose-binding domain (CBD), and glutathione S-transferase (GST).

In some cases, an AR-V inhibitor (e.g., an AR-V inhibitor oligonucleotide) provided herein can be in a delivery vehicle. Examples of delivery vehicles include, without limitation, gold nanoparticles, liposome, polymersomes, micelles, and plasmids.

In some cases, an AR-V inhibitor (e.g., an AR-V inhibitor oligonucleotide) provided herein can be formulated as a pharmaceutical composition. For example, a pharmaceutical composition containing an AR-V inhibitor provided herein can contain a pharmaceutically acceptable carrier for administration to a mammal, including, without limitation, sterile aqueous or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Acceptable carriers also can include physiologically acceptable aqueous vehicles (e.g., physiological saline) or other known carriers for oral administration.

An acceptable aqueous vehicle can be, for example, any liquid solution that is capable of dissolving an AR-V inhibitor (e.g., an AR-V inhibitor oligonucleotide) provided herein and is not toxic to the particular individual receiving the composition. Examples of acceptable aqueous vehicles include, without limitation, saline, water, and acetic acid. Typically, acceptable aqueous vehicles are sterile. An acceptable solid vehicle can be formulated such that compositions containing an AR-V inhibitor provided herein is suitable for oral administration. The dose supplied by each capsule or tablet can vary since an effective amount can be reached by administrating either one or multiple capsules or tablets. Any appropriate pharmaceutically acceptable material such as gelatin and cellulose derivatives can be used as an acceptable solid vehicle. In addition, an acceptable solid vehicle can be a solid carrier including, without limitation, starch, sugar, or bentonite. Further, a tablet or pill formulation of a composition containing an AR-V inhibitor provided herein can follow conventional procedures that employ solid carriers, lubricants, and the like. In some cases, a formulation of a composition containing an AR-V inhibitor provided herein can be formulated for controlled release.

Any appropriate method can be used to formulate a pharmaceutical composition provided herein (e.g., a pharmaceutical composition containing an AR-V inhibitor (e.g., an AR-V inhibitor oligonucleotide) provided herein). For example, common formulation mixing and preparation techniques can be used to make a pharmaceutical composition having the components described herein. In addition, the pharmaceutical compositions provided herein can be in any appropriate form. For example, a pharmaceutical composition provided herein can be in the form of a solid, liquid, and/or aerosol including, without limitation, powders, crystalline substances, gels, pastes, ointments, salves, creams, solutions, suspensions, partial liquids, sprays, nebulae, mists, atomized vapors, tinctures, pills, capsules, tablets, and gelcaps. In some embodiments, pharmaceutical compositions containing an AR-V inhibitor provided herein can be prepared for oral administration by mixing the components with one or more of the following: a filler, a binder, a disintegrator, a lubricant, and a coloring agent. Lactose, corn starch, sucrose, glucose, sorbitol, crystalline cellulose, silicon dioxide, or the like can be used as the filler. Polyvinyl alcohol, polyvinyl ether, ethyl cellulose, methyl cellulose, acacia, tragacanth, gelatin, shellac, hydroxypropyl cellulose, hydroxypropylmethyl cellulose, calcium citrate, dextrin, or pectin can be used as the binder. Magnesium stearate, talc, polyethylene glycol, silica, or hardened plant oil can be used as the lubricant. A pharmaceutically acceptable coloring agent can be used as the coloring agent. Cocoa powder, mentha water, aromatic acid, mentha oil, borneol, or powdered cinnamon bark also can be added. In some cases, pharmaceutical compositions containing an AR-V inhibitor provided herein can be prepared for injection by mixing the components with one or more of the following: a pH adjusting agent, a buffer, a stabilizer, and a solubilizing agent.

This document also provides methods for using an AR-V inhibitor (e.g., an AR-V inhibitor oligonucleotide) provided herein. Methods provided herein include administering to a mammal an AR-V inhibitor provided herein. In some cases, an AR-V inhibitor (e.g., a morpholino) provided herein can be administered to treat a mammal having cancer (e.g., prostate cancer such as CRPC). Administering an AR-V inhibitor provided herein to a mammal having cancer can be effective to reduce the number of and/or eliminate cancer cells in a mammal (e.g., human), to reduce and/or eliminate androgen-independent growth of CRPC cells, and/or to restore androgen responsiveness to a CRPC. In some cases, an AR-V inhibitor (e.g., a morpholino) provided herein can be used to modulate AR splicing. For example, an AR-V inhibitor provided herein can be used to inhibit non-canonical splicing of an AR pre-mRNA exon 3 to a CE within intron 3 (e.g., CE1, CE2, CE5, or CE3) and/or direct canonical splicing of an AR pre-mRNA exon 3 to a full-length AR. Administering an AR-V inhibitor provided herein can be effective to inhibit non-canonical splicing of AR transcripts, to reduce AR-V polypeptide expression, and/or to direct splicing to express full length AR.

An AR-V inhibitor (e.g., an AR-V inhibitor oligonucleotide) provided herein can be administered to any mammal (e.g., human, rat, mouse, dog, cat, horse, cow, goat, pig, or monkey). In addition, any route of administration (e.g., oral or parenteral administration) can be used to administer an AR-V inhibitor provided herein to a mammal. For example, an AR-V inhibitor provided herein can be administered orally or parenterally (e.g., a subcutaneous, intramuscular, intraorbital, intracapsular, intraspinal, intrasternal, or intravenous injection).

Cancer can occur in many tissues within the body. Examples of cancer that can be treated using an AR-V inhibitor (e.g., an AR-V inhibitor oligonucleotide) provided herein include, without limitation, prostate, breast, pancreatic, nasopharyngeal, ovarian, colon, colorectal, blood, lymph, lung, liver, brain, skin, and bone. In some embodiments, the cancer treated as described herein can be a prostate cancer. For example, the cancer treated as described herein can be a CRPC. Examples of ADT drugs that often result in the development of CRPC include, without limitation, antiandrogens (e.g., enzalutamide, abiraterone, flutamide, nilutamide, bicalutamide, apalutamide, finasteride, dutasteride, alfatradiol, and cyproterone acetate), and chemical castration (e.g., leuprolide, goserelin, triptorelin, histrelin, and degarelix). For example, an AR-V inhibitor provided herein can be used to treat a CRPC that developed following ADT treatment.

Methods for treating a mammal having cancer using an AR-V inhibitor (e.g., an AR-V inhibitor oligonucleotide) provided herein can be effective to reduce the number of cancer cells in the mammal. In some cases, treating a mammal having cancer using an AR-V inhibitor provided herein can be effective to eliminate the cancer cells in the mammal.

Methods for treating a mammal having cancer (e.g., prostate cancer) can include identifying the mammal as having cancer. Examples of methods for identifying the mammal as having cancer include, without limitation, physical examination, laboratory tests (e.g., blood, urine, and/or circulating tumor cells (CTCs)), biopsy, imaging tests (e.g., X-ray, PET/CT, MM, and/or ultrasound), nuclear medicine scans (e.g., bone scans), endoscopy, and/or genetic tests. In some cases, identifying the mammal as having prostate cancer (e.g., CRPC) can include, without limitation, testing blood, urine, and/or CTCs for PSA and/or one or more AR-Vs (e.g., AR-V7). Methods for treating a mammal having CRPC can include identifying said mammal as having a CRPC expressing one or more AR-V (e.g., AR-V7). Methods for treating a mammal having CRPC can include determining an AR-V (e.g., AR-V7) is expressed in the CRPC. Examples of methods for identifying if a CRPC expresses one or more AR-Vs and/or determining an AR-V expressed in a CRPC include, without limitation, reverse-transcriptase PCR, real-time PCR, northern blot analysis, western blot analysis, immunohistochemistry, whole genome sequencing, RNA sequence analysis, and/or tissue microarray analysis. Once identified as having cancer, the mammal can be administered or instructed to self-administer an AR-V inhibitor described herein.

Methods for treating a mammal by administering an AR-V inhibitor (e.g., an AR-V inhibitor oligonucleotide) provided herein also can include one or more additional cancer treatments such as surgery, hormone therapy (e.g., ADT), chemotherapy, radiation therapy, immunotherapy, and/or targeted therapy. Examples of ADT include, without limitation, antiandrogens (e.g., enzalutamide abiraterone, flutamide, nilutamide, bicalutamide, apalutamide, finasteride, dutasteride, alfatradiol, and cyproterone acetate), and chemical castration (e.g., leuprolide, goserelin, triptorelin, histrelin, and degarelix). Examples of chemotherapeutic drugs include, without limitation, alkylating agents (e.g., nitrogen mustards such as mechlorethamine, cyclophosphamide, melphalan, chlorambucil, ifosfamide and busulfan; nitrosoureas such as N-Nitroso-N-methylurea (MNU), carmustine (BCNU), lomustine (CCNU) and semustine (MeCNU), fotemustine and streptozotocin; tetrazines such as dacarbazine, mitozolomide and temozolomide; aziridines such as thiotepa, mytomycin and diaziquone (AZQ); cisplatins and derivatives such as cisplatin, carboplatin and oxaliplatin; and non-classical alkylating agents such as procarbazine and hexamethylmelamine), anti-metabolites (e.g., anti-folates such as methotrexate and pemetrexed; fluoropyrimidines such as fluorouracil and capecitabine; deoxynucleoside analogues such as cytarabine, gemcitabine, decitabine, Vidaza, fludarabine, nelarabine, cladribine, clofarabine and pentostatin; and thiopurines such as thioguanine and mercaptopurine), anti-microtubule agents (e.g., vinca alkaloids such as vincristine, vinblastine, vinorelbine, vindesine, and vinflunine; and taxanes such as paclitaxel, docetaxel, and cabazitaxel; podophyllotoxin; etoposide; and teniposide), topoisomerase inhibitors (e.g., topoisomerase I inhibitors such as irinotecan and topotecan; and topoisomerase II inhibitors such as etoposide, doxorubicin, mitoxantrone, teniposide, novobiocin, merbarone, and aclarubicin), and cytotoxic antibiotics (e.g., anthracyclines such as doxorubicin, daunorubicin, epirubicin, idarubicin, pirarubicin, aclarubicin, and mitoxantrone; bleomycins; mitomycin C; mitoxantrone; and actinomycin). In some cases, an AR-V inhibitor oligonucleotide provided herein can be formulated together with one or more additional cancer treatments (e.g., an ADT) to form a single composition. In some cases, one or more additional cancer treatments can be provided to a mammal in a separate composition; one containing an AR-V inhibitor oligonucleotide provided herein, and one containing, for example, an ADT. In cases where an AR-V inhibitor oligonucleotide provided herein and one or more additional cancer treatments are provided separately, the administration of an AR-V inhibitor provided herein can be in any order relative to the administration of one or more additional cancer treatments. For example, an AR-V inhibitor oligonucleotide provided herein can be administered to a mammal prior to, concurrent with, or following administration of one or more additional cancer treatments to the mammal. In cases where an AR-V inhibitor oligonucleotide provided herein is administered to a mammal following administration of an ADT (e.g., enzalutamide) to the mammal, the mammal can have CRPC and the AR-V inhibitor oligonucleotide can be effective to restore androgen responsiveness to the CRPC.

Any appropriate dose of an AR-V inhibitor (e.g., an AR-V inhibitor oligonucleotide) provided herein can be administered to a mammal. For example, an appropriate dose of an AR-V inhibitor provided herein can be effective to reduce the number of and/or eliminate cancer cells in a mammal (e.g., human), to reduce and/or eliminate androgen-independent growth of CRPC cells, to inhibit non-canonical splicing of AR transcripts, to reduce AR-V polypeptide expression, to direct splicing to express full length AR, and/or to restore androgen responsiveness to a CRPC upon administration to a mammal without producing significant toxicity to the mammal. Various factors can influence the actual amount used for a particular application. For example, the frequency of administration, duration of treatment, combination of other agents, site of administration, stage of disease (if present), and the anatomical configuration of the treated area may require an increase or decrease in the actual amount administered.

The frequency of administration of an AR-V inhibitor (e.g., an AR-V inhibitor oligonucleotide) provided herein can be any frequency. For example, the frequency of administration can be from about four times a day to about once a month, or more specifically, from about twice a day to about once a week. In addition, the frequency of administration can remain constant or can be variable during the duration of treatment. As with the amount administered, various factors can influence the actual frequency of administration used for a particular application. For example, the amount (dose), duration of treatment, combination of agents, site of administration, stage of disease (if present), and the anatomical configuration of the treated area may require an increase or decrease in administration frequency.

The duration of administration of an AR-V inhibitor (e.g., an AR-V inhibitor oligonucleotide) provided herein can be any duration. For example, a duration of administration of compositions provided herein can be longer than a week, month, three months, six months, nine months, a year, two years, or three years. In some cases, an effective duration can be any duration that reduces and/or eliminates the number of cancer cells, reduces and/or eliminates androgen-independent growth of CRPC cells, inhibits non-canonical splicing of AR transcripts, reduces AR-V polypeptide expression, directs splicing to express full length AR, and/or restores androgen responsiveness to CRPC cells upon administration to a mammal (e.g., human) without producing significant toxicity to the mammal. Such an effective duration can vary from several days to several weeks, months, or years. In general, an effective duration for the treatment of an acute disease can range in duration from several days to several months. Once administration of an AR-V inhibitor provided herein is stopped, however, symptoms may return. In such cases, an effective duration for the prevention of certain conditions can last for as long as the individual is alive. Multiple factors can influence the actual duration used for a particular treatment or prevention regimen. For example, an effective duration can vary with the frequency of administration, the amount administered, combination of multiple agents, site of administration, state of disease (if present), and anatomical configuration of the treated area.

The invention will be further described in the following examples, which do not limit the scope of the invention described in the claims.

EXAMPLES

Example 1

AR-V Expression in Castration Resistant Prostate Cancer

Long-read PacBio sequencing data indicated that CE3 was the terminal exon in transcripts where exon 3 spliced to CE1, CE2, and CE5 (data not shown), suggesting that the PAS in CE3 directs splicing of exon 3 to CE1, CE2, CE5, or CE3.

These results show that the PAS in CE3 directs splicing of exon 3 to CE1, CE2, CE5, or CE3.

Materials and Methods

Morpholino Design

Figure 2A:
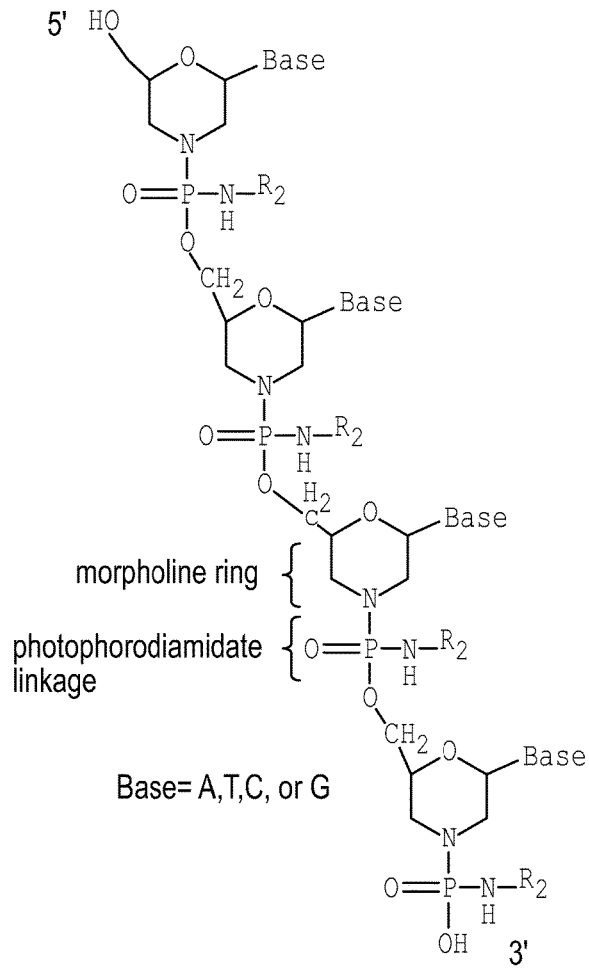
FIGS. 2A-2B show the structure and target site of an exemplary morpholino.
Figure 2B:
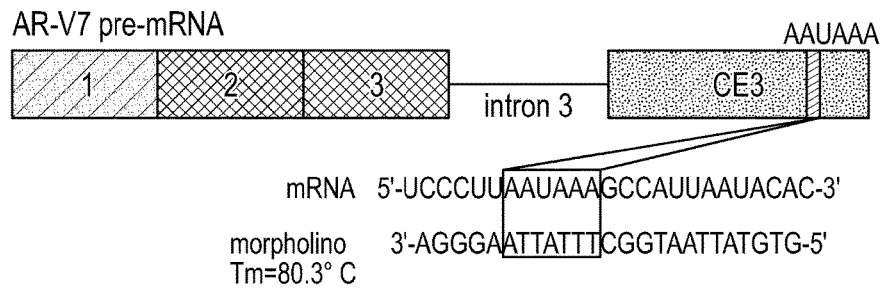

GeneTools' was used to design a morpholino, termed CE3 polyadenylation (poly A) mask (CE3 pAM) to block the CE3 poly A signal (FIG. 2A). CE3 pAM is a 25-mer consisting of the sequence 5'-GTGTATTAATGGCTTTAT-TAAGGGA-3' (SEQ ID NO:2), and binds with high affinity (Tm=80.3° C.) to the site 5'-UCCCUUAAUAAAGC-CAUUAAUACAC-3' (SEQ ID NO:4) in the AR CE3 sequence, which encompasses the poly A signal (AAUAAA, SEQ ID NO:3; FIG. 2B).

CE3 pAM was modified with an 8 guanidine head group (termed vivo-CE3 pAM) to promote uptake by cells, thereby functionalizing the morphilino to act as a drug-like small molecule. Vivo-CE3 pAM was designed and ordered using GeneTools' free design service.

Cell Culture, Transfection, and Drug Treatments.

E43 cells were cultured in RPMI-1640 and supplemented with 10% FBS and 500 μg/mL penicillin/streptomycin. For androgen blockade experiments, E43 cells were cultured in RPMI-1640 supplemented with 10% charcoal stripped FBS and 500 μg/mL penicillin/streptomycin. Transient transfections were performed using a BTX Square Wave electroporator. Transient transfection of E43 cells with the indicated concentration of CE3 pAM were carried out in RPMI-1640 supplemented with 10% FBS, and subsequently plated in appropriate culture medium. When appropriate, E43 cells were treated with 10 μM enzalutamide (MDV-3100, Selleck Chemicals) in indicated cell culture medium. E43 cells in cell culture medium were treated with vivo-CE3 pAM in 1X phosphate buffered saline at the indicated concentrations.

Crystal Violet Assays.

20,000 E43 cells transfected with 10 μM CE3 pAM or control morpholino were plated in 24-well dishes in the indicated culture medium and subjected to the indicated drug treatments. Crystal violet assays were performed on cells on days 2, 4, 6, 8, 11, and 14. Briefly, cells were fixed in 1% glutaraldehyde in 1X PBS and stained with 0.5% crystal violet in distilled water. At the end of the timecourse, fixed and stained cells were subjected to treatment with Sorenson's buffer (6.1 ml of 0.1 M disodium citrate, 3.9 ml of 0.1N HCl, and 10 ml of 95% ethanol) to release dye. Absorbance was measured at 560 nm.

Results

The CE3 pAM Morpholino Reduces Protein Levels of AR-Vs and Increases Protein Levels of Full-Length AR Transfection of E43 cells with CE3 pAM dramatically reduced expression of AR-V proteins including all four cryptic exons, CE1, CE2, CE3, and CE5, which encode AR-V1, AR-V5, AR-V7, and AR-V9 respectively (FIG. 3A). Transfection of E43 cells with CE3 pAM also redirected AR splicing to the normal PAS in exon 8 to increase expression of full-length AR (AR-FL) mRNA transcripts (FIG. 3A).

These results show that an AR-V inhibitor targeting the PAS in CE3 can be used to reduce protein expression of one or more AR-Vs, and to increase expression of full length AR proteins.

The CE3 pAM Morpholino Reduces mRNA Levels of AR-Vs and Increases mRNA Levels of Full-Length AR Transfection of E43 cells with CE3 pAM blocked expression of AR-V2, AR-V5, AR-V7, and AR-V9, which are encoded by AR exon 3 splicing to AR exons CE1, CE2, CE3, or CE5, respectively (FIG. 3B).

These results show that an AR-V inhibitor targeting the PAS in CE3 can be used to reduce mRNA of one or more AR-Vs, and to increase expression of full length AR mRNA.

The CE3 pAM Morpholino Reduced Androgen-Independent Growth of Castration Resistant Prostate Cancer Cell Lines Transfection of E43 cells with CE3 pAM reduced AR-V expression inhibited cell growth of E43 cells cultured under conditions modeling maximum androgen blockade castration+enzalutamide, but not under androgenic conditions where full-length AR would remain active (FIG. 3C). In growth medium containing charcoal stripped serum (androgen replete), e43 cells transfected with CE3 poly A mask and treated with 10 uM enzalutamide exhibit a significant reduction (~50%) in cell growth assessed by crystal violet staining (FIG. 3C).

These results show that an AR-V inhibitor targeting the PAS in CE3 can be used to restore androgen responsiveness to a CRPC.

Vivo-CE3 pAM Morpholino is Taken Up by Cells

Figure 4:
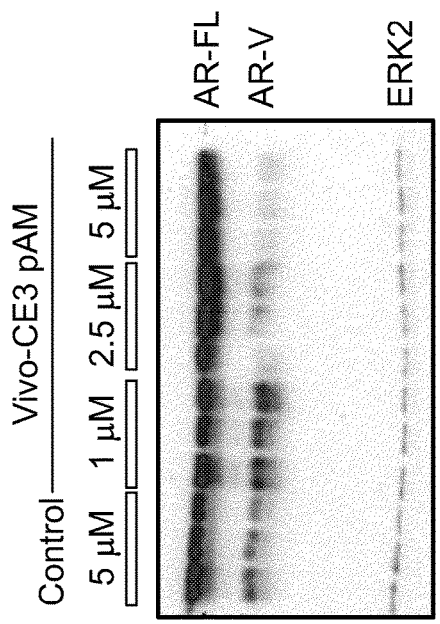
FIG. 4 shows that treatment of E43 cells with vivo-CE3 pAM inhibits AR-V protein expression and increases AR-FL protein levels.

Addition of vivo-CE3 pAM to tissue culture medium inhibited expression of AR-Vs and enhanced expression of AR-FL in cells when added at a final concentration of 2.5-5 μM (FIG. 4).

These results show that an AR-V inhibitor targeting the PAS in CE3 can be taken up by cells to inhibit expression of AR-Vs.

Summary

Together these results demonstrate that an AR-V inhibitor targeting an upstream PAS (e.g., in intron 3) represents an effective therapeutic strategy to reduce multiple AR-V mRNA and protein species, thereby reducing androgen-independent growth of CRPC cells. These results also demonstrate that an AR-V inhibitor can restore androgen responsiveness to a CRPC, and can be used in combination with ADT (e.g., enzalutamide).

Example 2

Targeting a Single Alternative Polyadenylation Site to Coordinately Block Expression of Androgen Receptor mRNA Splice Variants in Prostate Cancer Cells Genome engineering was used to develop models of AR-V7-positive CRPC that more accurately reflected AR-V7 expression levels observed in clinical CRPC. Interrogation of these models demonstrated that splicing of AR-V7 occurred coordinately with splicing of additional AR-Vs, and that all of these splicing events were regulated by a single polyadenylation signal residing in AR intron 3. Morpholino technology was used to interfere with this AR alternative polyadenylation mechanism, and to inhibit expression and function of AR-Vs in CRPC.

Materials and Methods

Cell Culture

22Rv1 cells (CRL-2505) were obtained from ATCC (Manassas, Va., USA) and cultured according to ATCC protocol. LNCaP95 cells were cultured in phenol red free RMPI 1640 (Invitrogen) supplemented with 10% fetal bovine serum and 1× penicillin/streptomycin. VCaP cells (ATCC CRL-2876) were cultured in DMEM medium (Invitrogen) supplemented with 10% fetal bovine serum and 1× penicillin/streptomycin. ATCC authenticates human cell lines using short tandem repeat analysis. Cell lines were routinely monitored for mycoplasma infection by regularly evaluating aliquots of supernatants from cells in culture for mycoplasma contamination using a PCR-based method as described elsewhere (see, e.g., Uphoff et al., 2012, *J. Biomed. Biotechnol.*, 2012:267678).

Genetic Correction of AR in 22Rv1

Construction of tAR2 TALENs was carried out as described elsewhere (see, e.g., Nyquist et al., 2013, *Proc. Natl. Acad. Sci. USA*, 110:17492-7). Repeat variable dinucleotide (RVD) modules used to generate tAR2 plasmids are listed in Table 1.

TABLE 1

Illumina HiSeq Sequencing metrics per sample.

| raw_or_pf | read | lane | sample id | barcode | yield | yield_q30 | Reads |
|---|---|---|---|---|---|---|---|
| pf | 1 | 6 | E43-2 | AAAGCA | 1,203,648,209 | 1,090,353,265 | 11,917,309 |
| pf | 2 | 6 | E43-2 | AAAGCA | 1,203,648,209 | 1,057,768,408 | 11,917,309 |
| pf | 1 | 6 | B34-4 | GAAACC | 1,269,183,473 | 1,155,970,661 | 12,566,173 |
| pf | 2 | 6 | B34-4 | GAAACC | 1,269,183,473 | 1,125,244,000 | 12,566,173 |

TABLE 1-continued

Illumina HiSeq Sequencing metrics per sample.

| raw_ or_ pf | quality score sum | Calculated average Q-Score | Reads PF | Reads Raw | Calculated percent reads PF | Calculated barcode percentage in lane |
|---|---|---|---|---|---|---|
| pf | 42,745,880,386 | 35.51 | 11,917,309 | 11,917,309 | 100 | 6.02 |
| pf | 41,713,131,234 | 34.66 | 11,917,309 | 11,917,309 | 100 | 6.02 |
| pf | 45,316,527,409 | 35.71 | 12,566,173 | 12,566,173 | 100 | 6.35 |
| pf | 44,337,293,235 | 34.93 | 12,566,173 | 12,566,173 | 100 | 6.35 |

To generate 22Rv1 duplication-corrected subclones, cells were electroporated with tAR2 vectors and a single strand annealing (SSA) reporter, pJET: mCherry-PGK-EF1a-GFPssa. The SSA reporter was constructed using conventional cloning into the pJET1.2 vector (Clontech, #K1231). The PGK-EF1a is a bidirectional promoter that expresses mCherry from the PGK promoter and a GFPssa construct from the EF1a promoter. The GFPssa consists of the first 445 bp of GFP, a SalI-SacI cloning site for annealed TALEN cutsite oligos, and the last 605 bp of GFP including a 330 bp overlap region. Cells with TALEN nuclease activity were identified by GFP positivity and sorted by flow cytometry into single wells of 96 well plates. Clones were screened by PCR and restriction enzyme digestion of the PCR products to detect disruption of an Afl III restriction enzyme site in the tAR-2 spacer sequence. Subclones lacking this Afl III site were further screened by multiplex ligation-dependent probe amplification (MLPA) as described elsewhere (see, e.g., Li et al., 2012 Oncogene, 31:4759-67). Genomic DNA was isolated using Nucleospin tissue kit (Catalog 740952, Machery-Nagel). Genomic DNA was amplified using Phusion-HF (M0530S New England Biolabs, Ipswich, Mass.) according to the manufacturer protocol and the following primers: AR int2 F1: 5'-CTCCCAACAAGTGATCAGTAGTCA-GAAAATGG-3' (SEQ ID NO:11), AR int2 R1: 5'-CAACA-GGGTATCTTATTTTGCAAACCCTAAGTC-3' (SEQ ID NO:12). Products were cloned and sequenced as previously described (see, e.g., Nyquist et al., 2013, Proc. Natl. Acad. Sci. USA, 110:17492-7). Genomic PCR products were column purified with Qiaquick PCR purification kit (28104 Qiagen, Valencia, Calif.) and digested with 10 units of Afl III (R05415 New England Biolabs, Ipswich, Mass.) for 2 hours. Restriction analysis was performed via agarose gel electrophoresis.

siRNA Transfections

For siRNA transfections, cells in medium supplemented with 10% charcoal-stripped FBS were mixed with 200 pmol targeted or nontargeting control siRNAs (Dharmacon). siRNAs were obtained from Dharmacon: nontargeting negative control (D-001210-01), CPSF1 smartpool: M-020395-01-0005 CPSF1 individual siRNAs: D-020395-01-0002, D-020395-02-0002, D-020395-03-0002, D-020395-04-0002, CPSF2 smartpool (M-013404-00-0005), CPSF3 smartpool (M-006365-00-0005), CPSF4 smartpool (M-012292-02-0005), WDR33 smartpool (M-017101-02-0005), FIP1L1 smartpool (M-014670-00-0005), U2AF2 (L-012380-02), SRSF1 (L-018672-01), PTBP1 (L-003528-00). siRNA sequences designed to target AR CE3 were as follows: siCE3-01: 5'-GUAGUUGUGAGUAUCAUGA-3' (SEQ ID NO:13), siCE3-02: SENSE: 5'-AGGACGGGCU-GUAGAAGUAUU-3' (SEQ ID NO:14), ANTISENSE: 5'-UACUUCUACAGCCCGUCCUUU-3' (SEQ ID NO:15), siCE3-03: SENSE: 5'-CAAAAUGACCAGACCCUGAUU-3' (SEQ ID NO:16), ANTISENSE: 5'-UCAGGGUCUGGU-CAUUUUGUU-3' (SEQ ID NO:17).

Cell/siRNA mixtures were electroporated in a 4-mm gap-width cuvette (BTX) with a BTX Square Wave Electroporator (22Rv1 and sublines: 350 V, 10 ms pulse, LNCaP95: 305 V, 10 ms pulse). Following a 15-minute recovery, cells were seeded in appropriate culture medium. VCaP cells were transfected with Lipofectamine 2000 according to manufacturer instructions.

Morpholino Transfections

GeneTools' design tool was used to design a 25-mer consisting of the sequence 5'-GTGTATTAATGGCTTTAT-TAAGGGA-3' (SEQ ID NO:2) targeted to the CE3 PAS (CE3 pAM). As a control, a standard commercially available nontargeting control morpholino was used (GeneTools). Morpholinos were labeled with 3' fluorescein to visualize transfection efficiency. For morpholino transfections, cells were mixed with 10 μM CE3 pAM or control morpholino, electroporated, and seeded in culture dishes as described above. For VCaP and LNCaP 95 studies, Vivo-morpholinos (GeneTools) functionalized for cellular uptake were designed as 25-mer sequences corresponding to the same sequences for control and CE3 pAM and added at a final concentration of 1 μM directly to medium supplemented with 5% FBS and 1× penicillin/streptomycin.

Western Blots

Cells were lysed in 1× Laemmli buffer (65 mmol/L Tris-HCl (pH 7.0), 2% (w/v) SDS, 5% β-mercaptoethanol, 10% (v/v) glycerol, and 0.5% (w/v) bromophenol blue). Equal volumes of lysates were loaded onto 4-20% or 7.5% PAGE gels (TGX, Biorad) and electrophoresed in 1×SDS PAGE running buffer, followed by transfer to PVDF membrane (Immobilon-P, Millipore).

For AR subcellular fractionation, 22Rv1-undup3 cells were seeded in RPMI medium supplemented with 10% CSS for 24 hours and treated with either ethanol (vehicle) or 1 nM mibolerone (synthetic androgen) for 24 hours. Cells were washed with 1×PBS, harvested in hypotonic buffer, and subjected to subcellular fractionation as described elsewhere (see, e.g., Chan et al., 2012, J. Biol. Chem., 287: 19736-49). Lysates in 1× Laemmli buffer were loaded in equal volumes on either 7.5% or 4-15% polyacrylamide gels (Biorad TGX) and electrophoresed at 200v for 30 minutes.

Blots were incubated with antibodies specific to CPSF1 (Bethyl, A301-580, 1:1000), AR (Santa Cruz Santa Cruz Biotechnology N-20, 1:2000), extracellular signal-regulated kinase-2 (ERK-2; Santa Cruz Biotechnology D-2, 1:4000), and AR-V7 (Precision Antibodies, 1:1000). HRP-conjugated goat-anti-mouse (#sc 2005, lot#D1515), and goat-anti-rabbit (#sc 2004, lot#B1315) secondary antibodies were obtained from Santa Cruz and were used at 1:10000 dilutions. Blots were incubated in enhanced chemiluminescence substrate (WesternBright, Advansta #K12045-D50 or SuperSignal West Pico, Thermo #1859674) and exposed to X-ray film for chemiluminescence detection.

RNA Purification and Reverse Transcription

RNA was isolated from cells using the Reliaprep RNA Miniprep System (Promega) and purified according to kit manufacturer instructions, including a 30-minute room temperature DNase treatment. RNA was eluted in nuclease free water. RNA concentration and integrity were assessed by denaturing gel electrophoresis or by spectrophotometry with a NanoDrop 2000 (ThermoFisher). Reverse transcription was performed using the GoScript Reverse Transcription kit (Promega) with 0.5-5 µs input RNA and random hexamers according to manufacturer instructions.

Quantitative PCR

Quantitative PCR was performed using Quanta PerfeCTa master mix, 200 nM forward and reverse primers, and 2 µL input cDNA (serially diluted in nuclease free water 1:50 for 18S samples) in 20 µL reactions. Negative controls included no-template and no-RT reactions for each primer set. Cycling conditions were: i. 95° C. for 3 minutes, ii. 95° C. for 15 seconds, iii. 60° C. for 30 seconds. Steps ii-iii were repeated for a total of 40 cycles. All PCR reactions were subjected to thermal melting to confirm that each reaction gave single peaks. All reactions were carried out in technical duplicate, with at least two biological replicates. Quantitative PCR was performed on a BioRad CFX Connect Real-Time PCR Detection System or a BioRad MyiQ Single Color Real-Time PCR Detection System. Cycle thresholds (Ct) were determined using the Biorad CFX manager software. Changes in mRNA expression were calculated by $\Delta\Delta Ct = \Delta Ct_{target} - \Delta Ct_{control}$. Relative changes in mRNA expression levels are represented graphically as fold changes, wherein relative mRNA fold change=$2^{-\Delta\Delta Ct}$. All statistical tests were performed in GraphPad. qPCR primer sequences are as described below.

For AR target gene assessment, primers were as follows:

```
GAPDH fwd:
                                    (SEQ ID NO: 18)
5'-GAAGGTGAAGGTCGGAGTC-3', GAPDH rev:
                                    (SEQ ID NO: 19)
5'-GAAGATGGTGATGGGATTTC-3', PSA fwd:
                                    (SEQ ID NO: 20)
5'-AGGCCTTCCCTGTACACCAA-3', PSA rev:
                                    (SEQ ID NO: 21)
5'-GTCTTGGCCTGGTCATTTCC-3', TMPRSS2 fwd:
                                    (SEQ ID NO: 22)
5'-CTGCCAAGGTGCTTCTCATT-3', TMPRSS2 rev:
                                    (SEQ ID NO: 23)
5'-CTGTCACCCTGGCAAGAATC-3', FKBP5 fwd:
                                    (SEQ ID NO: 24)
5'-AGGAGGGAAGAGTCCCAGTG-3', FKBP5 rev:
                                    (SEQ ID NO: 25)
5'-TGGGAAGCTACTGGTTTTGC-3', hK2 fwd:
                                    (SEQ ID NO: 26)
5'-CTGTCAGAGCCTGCCAAGAT-3', hK2 rev:
                                    (SEQ ID NO: 27)
5'-GCAAGAACTCCTCTGGTTCG-3'.
```

For splicing factor knockdown and assessment of AR-V7 and total AR levels, the following primers were used:

```
GAPDH fwd:
                                    (SEQ ID NO: 18)
5'-GAAGGTGAAGGTCGGAGTC-3', GAPDH rev:
                                    (SEQ ID NO: 19)
5'-GAAGATGGTGATGGGATTTC-3', AR exon 1 fwd:
                                    (SEQ ID NO: 28)
5'-TGGATGGATAGCTACTCCGG-3', AR exon 2 rev:
                                    (SEQ ID NO: 29)
5'-CCCAGAAGCTTCATCTCCAC-3', AR exon 3 fwd:
                                    (SEQ ID NO: 30)
5'-AACAGAAGTACCTGTGCGCC-3', AR CE3 rev:
                                    (SEQ ID NO: 31)
5'-TCAGGGTCTGGTCATTTTGA-3', SRSF1 fwd:
                                    (SEQ ID NO: 32)
5'-GAAACTGCCTCAATCCGGGT-3', SRSF1 rev:
                                    (SEQ ID NO: 33)
5'-GTAACTGCGACTCCTGCTGT-3', U2AF2 fwd:
                                    (SEQ ID NO: 34)
5'-CAGGCCTCACGACTACCAG-3', U2AF2 rev:
                                    (SEQ ID NO: 35)
5'-GGGACCACAGTGGACACAA-3', PTBP1 fwd:
                                    (SEQ ID NO: 36)
5'-CGGGGATCTGACGAGCTTTT-3', PTBP1 rev:
                                    (SEQ ID NO: 37)
5'-TCGGCTGTCACCTTTGAACT-3'.
```

For AR-V7 RNAi, CPSF complex RNAi, and morpholino experiments, the following primers to detect AR-Vs and full length AR were used:

```
AR exon 3 fwd:
                                    (SEQ ID NO: 30)
5'-AACAGAAGTACCTGTGCGCC-3', CE1 rev:
                                    (SEQ ID NO: 38)
5'-TGAGACTCCAAACACCCTCA-3' (AR-V1),
```

```
CE2 rev:
                                        (SEQ ID NO: 39)
5'-TATGACACTCTGCTGCCTGC-3' (AR-V6), CE5 rev:
                                        (SEQ ID NO: 40)
5'-GCAAATGTCTCCAAAAAGCAGC-3' (AR-V9).
```

AR-V7 was detected with:

```
AR exon 3 fwd2:
                                        (SEQ ID NO: 41)
5'-CGGAAATGTTATGAAGCAGGGATGACTC-3', CE3 rev:
                                        (SEQ ID NO: 42)
5'-CCAGACTATCCACTAGAGCCCTCT-3'.
```

Primers used in this study to detect full length AR included:

```
AR Ex7 fwd:
                                        (SEQ ID NO: 43)
5'-TACCAGCTCACCAAGCTCCTG-3', AR Ex8 rev:
                                        (SEQ ID NO: 44)
5'-GAAAGTCCACGCTCACCATGTG-3'.
```

For CPSF complex siRNA screening, the following primers were used:

```
CPSF1 fwd:
                                        (SEQ ID NO: 45)
5'-GTGTACAAACAGGCGCATCC-3', CPSF1 rev:
                                        (SEQ ID NO: 46)
5'-TCATTCTTGGTCAGAGCCTCG-3', CPSF2 fwd:
                                        (SEQ ID NO: 47)
5'-GAGGCCTGACGAGATTAATAAAGA-3', CPSF2 rev:
                                        (SEQ ID NO: 48)
5'-AGGGCAGATTCTTCTTGGACC-3', CPSF3 fwd:
                                        (SEQ ID NO: 49)
5'-GGAGTGACGGAAGTTGTGCT-3', CPSF3 rev:
                                        (SEQ ID NO: 50)
5'-AGCTCCAAGGGGTCGGATCA-3', CPSF4 fwd:
                                        (SEQ ID NO: 51)
5'-CCCTCGATTTGAACTGCCCA-3', CPSF4 rev:
                                        (SEQ ID NO: 52)
5'-TCCTTTCTCGCCACACTTGTA-3', WDR33 fwd:
                                        (SEQ ID NO: 53)
5'-GAGCGGGATTGAGAGGATCG-3', WDR33 rev:
                                        (SEQ ID NO: 54)
5'-TAGGATACGTCTGGCTTTGAGC-3', FIP1L1 fwd:
                                        (SEQ ID NO: 55)
5'-GGAGCACCACAGTATGGGAG-3', FIP1L1 rev:
                                        (SEQ ID NO: 56)
5'-ATCAGCACCAGGTTTACGCC-3'.
```

CPSF complex knockdown experiments used 18S primers as an internal control as described elsewhere (see, e.g., Van Etten et al., 2012 *J. Biol. Chem.*, 287:36370-83). The sequences were as follows:

```
18S fwd:
                                        (SEQ ID NO: 57)
5'-CAGCCACCCGAGATTGAGCA-3', 18S rev:
                                        (SEQ ID NO: 58)
5'-TAGTAGCGACGGGCGGTGTG-3'.
```

As internal controls, AR-V7 siRNA and morpholino experiments used

```
Actin2 fwd:
                                        (SEQ ID NO: 59)
5'-ATGCAGAAAGAGATCACCGC-3', Actin2 rev:
                                        (SEQ ID NO: 60)
5'-ACATCTGCTGGAAGGTGGAC-3'.
```

Mean mRNA fold change for each target gene is shown throughout the manuscript. Error bars for qPCR experiments indicate 95% confidence intervals. Mean mRNA fold changes relative to controls were subjected to unpaired t-tests. All statistical analyses were performed in GraphPad.

Cell Growth Assays

Electroporated 22Rv1 cells and sublines were seeded at 20,000 cells per well in 24 well dishes in RPMI 1640 supplemented with 10% charcoal-stripped FBS. Twenty-four hours after seeding, medium was exchanged with RPMI 1640 medium containing 10% charcoal stripped FBS supplemented with 1 nM dihydrotestosterone (DHT) or vehicle control (ethanol). Crystal violet staining assays were performed as described elsewhere (see, e.g., Li et al., 2013, *Cancer Res.*, 73:483-9) and absorbance was measured at 560 nm. Significance was assessed by two tailed t-tests in GraphPad.

AR RNA Sequencing

For AR RNA-seq, RNA isolated from 22Rv1 cells was subjected to reverse transcription using the Clontech Advantage RT kit using both oligo-dT and random hexamer primers as per the manufacturer's recommendations. cDNA samples were submitted to the University of Minnesota Genomics Center for RNA-seq library preparation and hybrid capture with a custom AR-based SureSelect (Agilent) bait library (Li et al., *Oncogene*, 31:4759-67) using the SureSelect QXT reagent kit (Agilent) as per manufacturer's recommendations.

For data analyses, sequencing libraries were pooled and diluted to 10 pM for flow cell clustering and sequenced using Illumina HiSeq 2000 with 2×50 bp settings. Illumina reads were aligned to hg19 using TopHat (v.2.0.11; Kim et al., 2011, *Genome Biol.*, 12):R72) with—no-coverage-search and—micro-exon-search enabled, and the mean and standard deviation for the inner distance between mate pairs set empirically. AR and AR-V isoforms have been annotated (Lu et al., 2013, *Transl. Androl. Urol.*, 2:178-86). Annotated AR and AR-V isoforms from the UCSC annotation database were used as a guide for TopHat alignment. Aligned reads in .bam format were visualized in IGV. The TopHat junctions- .bed output file was parsed to determine how many reads supported novel and canonical splice junctions within the AR locus.

AR DNA Sequencing

Genomic DNA isolated from isogenic gene corrected sub-lines 22Rv1-undup1 and 22Rv1-undup3 was submitted to the University of Minnesota Genomics Center for DNA-seq library preparation and hybrid capture as described elsewhere (see, e.g., Li et al., 2012 *Oncogene*, 31:4759-67). LUMPY and DELLY structural variant callers were employed as described elsewhere (see, e.g., Henzler et al., 2016, *Nature Communications*, 7:13668). Freebayes and Varscan were used to detect mutations in 22Rv1 sub-lines as described elsewhere (see, e.g., Henzler et al., 2016, *Nature Communications*, 7:13668).

Analysis of CPSF Complex Alterations in Primary and Metastatic Prostate Cancer

Publicly available datasets were queried using cBioPortal (Cerami et al., 2012, *Cancer Discov.*, 2:401-4) to ascertain whether the CPSF complex exhibited changes in mRNA abundance, copy number, and mutation status from both primary (Abeshouse et al., 2015 *Cell*, 163:1011-25) and metastatic prostate cancer (Robinson et al., 2015, *Cell*, 161:1215-28). Mutual exclusivity plots were generated in Excel from scores of mutual exclusivity or co-occurrence obtained from cBioPortal.

TCGA RNA-seq Analysis

Raw RNA-seq data from the TCGA prostate cancer dataset was downloaded from the NCBI database of genotypes and phenotypes (dbGaP; Cancer Genome Atlas Research Network, 2015, *Cell*, 163:1011-25), study accession phs000178.v9.v8, yielding paired tumor/normal samples for 52 patient samples.

Genes under 300 bp were removed from further analysis as these are not isolated effectively in standard RNA-seq library preps. Genes with low expression (those with less than 10 reads in half of the samples) were removed, and paired tumor and normal samples were analyzed for differential expression using edgeR. In edgeR, the ROAST gene set test was used to test whether known splicing genes were differentially expressed in the cancer samples (Wu et al., 2010, *Bioinformatics*, 26:2176-82).

Su2C RNA-seq Analysis

RNA-seq data from the AACR-PCF Stand-Up-To-Cancer study of metastatic CRPC biopsies was obtained from the NCBI dbGaP (Cancer Genome Atlas Research Network, 2015, *Cell*, 163:1011-25), study accession phs000554.v1.p1. RNA-seq Illumina reads were aligned to hg19 using TopHat (v.2.0.11) with —no-coverage-search and —micro-exon-search enabled, and the mean and standard deviation for the inner distance between mate pairs set empirically (Kim et al., 2011, *Genome Biol.*, 12:R72). Annotated AR and AR-V isoforms from the UCSC annotation database were used as a guide for TopHat alignment. Aligned reads in .bam format were visualized in integrative genomics viewer (IGV) (Robinson et al., 2011, *Nat. Biotechnol.*, 29:24-6). The TopHat junctions.bed output file was parsed to determine how many reads supported novel and canonical splice junctions within the AR locus.

Results and Discussion

AR Gene Correction in 22Rv1 Cells

Figure 5A:
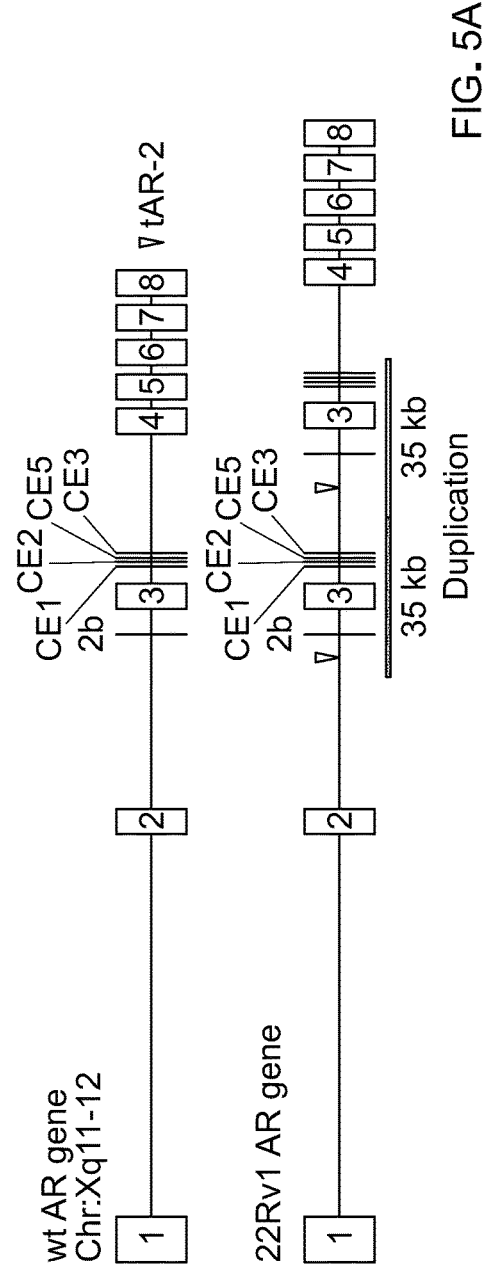
FIGS. 5A-5D show AR gene correction in 22Rv1 cells.
Figure 6A:
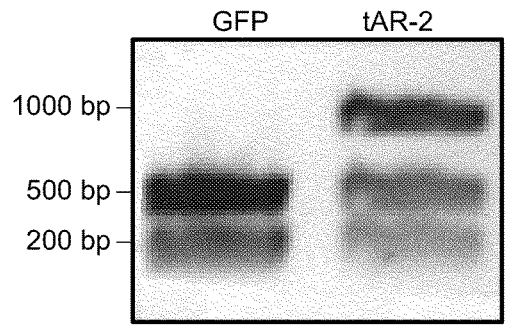
FIGS. 6A-6B show TALEN activity and genetic correction of 22Rv1 sub-lines.

The CRPC 22Rv1 cell line harbors a 35 kb tandem duplication encompassing AR exon 3 and cryptic exons (CEs) that are spliced as the alternative 3' terminal exons of AR-Vs including AR-V7 (Li et al., 2011, *Cancer Res.*, 71:2108-17). To determine whether removal of this duplication would eliminate or dramatically reduce AR-V7 expression, transcription activator-like effector nucleases (TALENs), termed tAR-2, were used to cut DNA in two regions flanking the duplication (FIG. 5A, FIG. 6A).

Figure 5B:
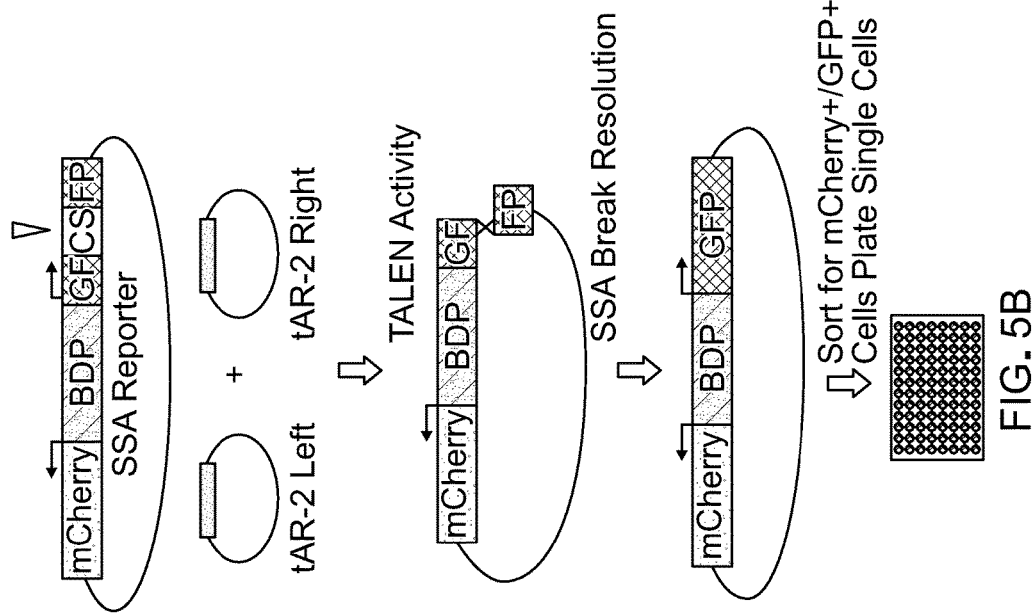
Figure 6B:
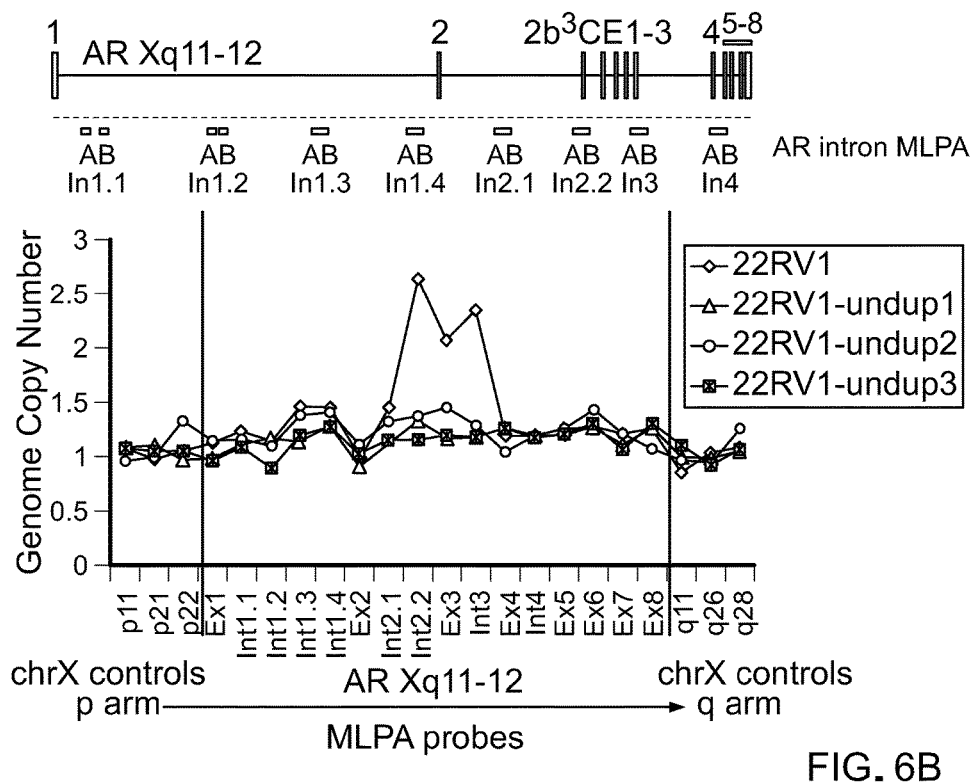

A bidirectional mCherry/GFP reporter plasmid was used to enrich cells displaying tAR-2 activity (FIG. 5B). mCherry+/GFP+ cells were screened by PCR (FIG. 6A), and assessed for AR gene copy number using multiplex ligation-dependent probe amplification (FIG. 6B). This yielded three 22Rv1 sub-lines, termed 22Rv1-undup1, -undup2, and -undup 3. PCR isolation of break fusion junctions confirmed that 22Rv1-undup1-3 arose from TALEN engineering, as they contained DNA inserted from the bidirectional reporter or tAR-2 plasmids (FIG. 7). Paired-end sequencing of AR in 22Rv1-undup1 and 22Rv1-undup3 cells (Table 2) ruled out alternative rearrangements while confirming the parental 22Rv1 H874Y mutation (Table 3).

TABLE 2

Repeat variable dinucleotide (RVD) modules used to create tAR2 left and right TALENs.

| RVD position | 1 | 2 | 3 | 4 | 5 | 6 | 7 | 8 | 9 | 10 | 11 | 12 | 13 | 14 | 15 | Target site |
|---|---|---|---|---|---|---|---|---|---|---|---|---|---|---|---|---|
| tAR2 Left | NN | NI | NI | HD | NI | NG | NG | HD | HD | NG | NN | HD | HD | NG | NN | gaacattcctgcctggctgacatgtggactctctgaaattgttat (SEQ ID NO: 61) |
| tAR2 Right | NI | NG | NI | NI | HD | NI | NI | NG | NG | NG | HD | NI | NN | NI | NN | |

TABLE 3

Mean per-base read coverage and copy number of the AR gene for 22Rv1 sub-lines.

| Sample ID | Type | Mean per-base read coverage of AR | AR copy number | AR bases with zero coverage | AR bases with coverage |
|---|---|---|---|---|---|
| 22Rv1-undup1 | met | 347 | 1 | 36377 | 150211 |
| 22Rv1-undup3 | met | 325 | 1 | 39932 | 146656 |

These results demonstrated that 22Rv1-undup1-3 were bona fide AR gene-corrected sub-lines of 22Rv1.

Functional AR-V7 Expression in AR Gene-corrected 22Rv1 Cells

Figure 5C:
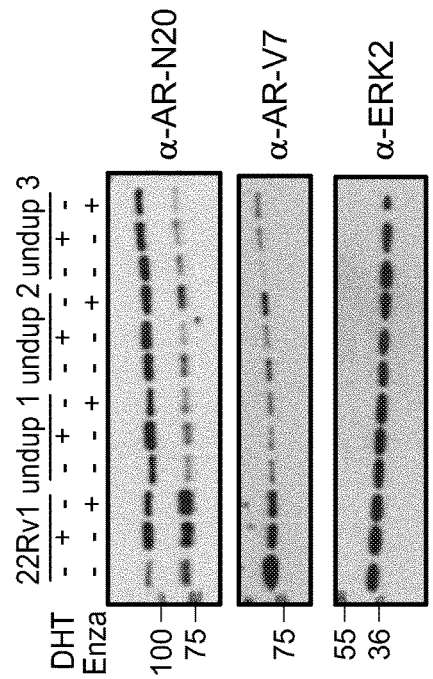

Parental 22Rv1 and 22Rv1-undup1-3 sub-lines expressed full length AR (AR-FL) at similar levels under castrate or DHT-stimulated conditions, and after treatment with the AR antagonist enzalutamide (FIG. 5C). Conversely, 22Rv1-undup1-3 sub-lines displayed reduced AR-V7 expression (FIG. 5C). AR-FL electrophoretic mobility in 22Rv1-undup1-3 lysates was faster, consistent with AR-FL no longer harboring an extra zinc-finger in the DNA binding domain due to the 22Rv1 tandem duplication (Li et al., 2011,

*Cancer Res.*, 71:2108-17). Additionally, AR-FL in 22Rv1-undup3 cells displayed strong nuclear localization upon stimulation with 1 nM of the synthetic androgen mibolerone, indicating normal nuclear translocation (FIG. 8). These data confirmed that AR gene rearrangements were driving AR-V overexpression in 22Rv1 cells. However, AR-V7 expression was not abolished, suggesting a rearrangement-independent mechanism of AR-V7 synthesis.

Figure 5D:
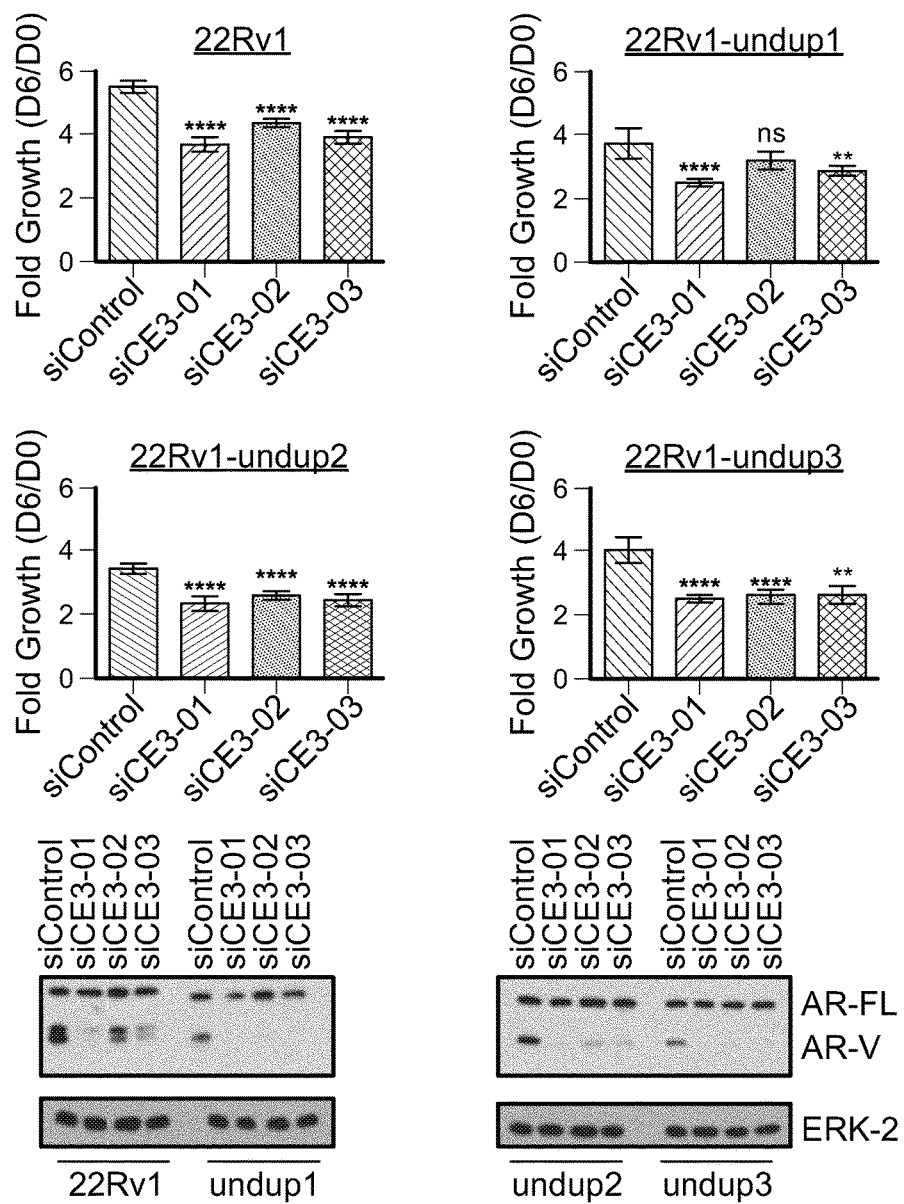
Figure 9D:
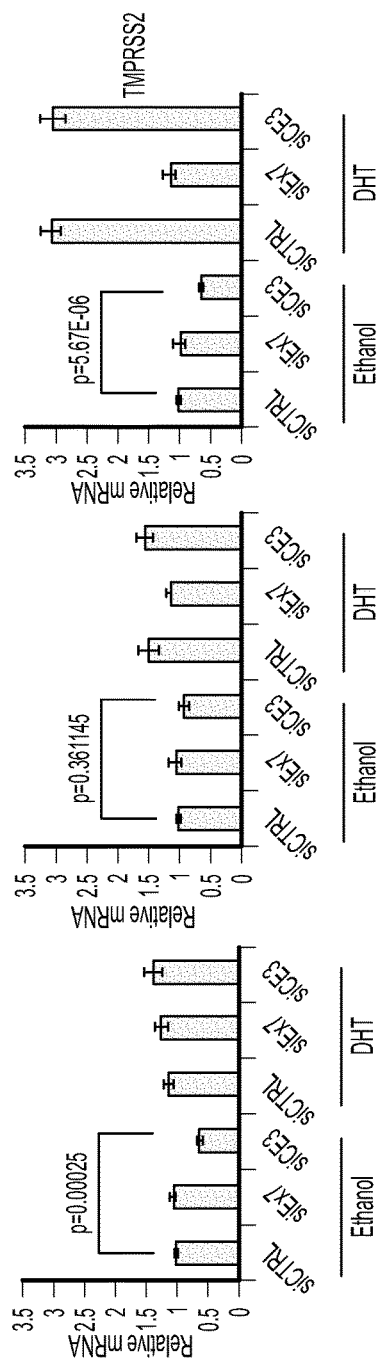
Figure 9E:
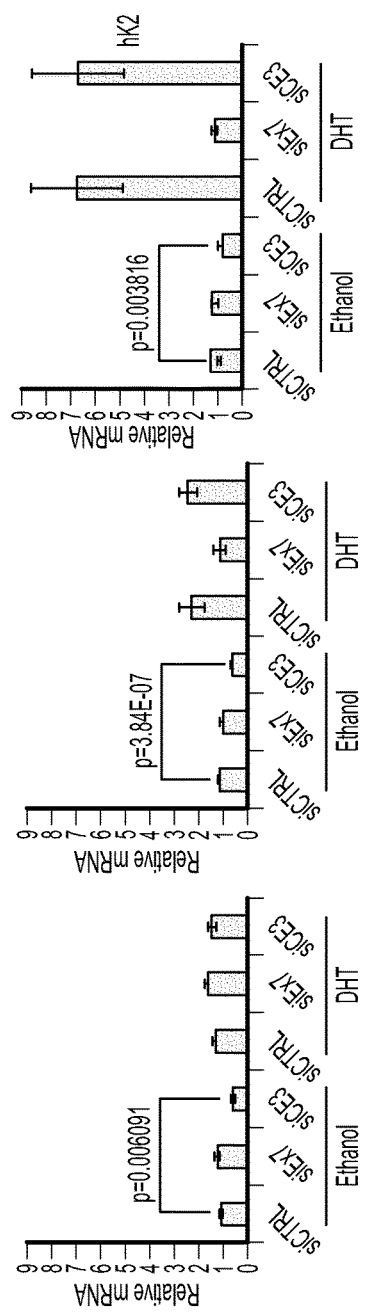

Knockdown of AR-V7 in 22Rv1-undup1-3 sublines using siRNAs targeted to CE3 reduced expression of AR transcriptional targets FKBP5, PSA, TMPRSS2, and hK2 under castrate conditions (FIG. 9). Additionally, knockdown of AR-V7 inhibited androgen-independent growth (FIG. 5D). Collectively, these findings indicated that AR-V7 in 22Rv1-undup1-3 sub-lines was expressed at much lower levels than parental 22Rv1 cells, but this expression remained sufficient for AR-V7 to transcriptionally activate AR target genes and support growth in the absence of androgens.

Regulation of AR Splicing by Alternative Polyadenylation

To understand the mechanisms regulating AR-V7 expression in 22Rv1-undup-1-3 sub-lines, CE3 splice acceptor site recognition was assessed. We knocked down splicing factors U2AF2, SRSF1, and PTBP1 and found that they did not specifically inhibit expression of endogenous AR-V7 in 22Rv1 or 22Rv1-undup1-3 sub-lines (FIG. 10).

Figure 11A:
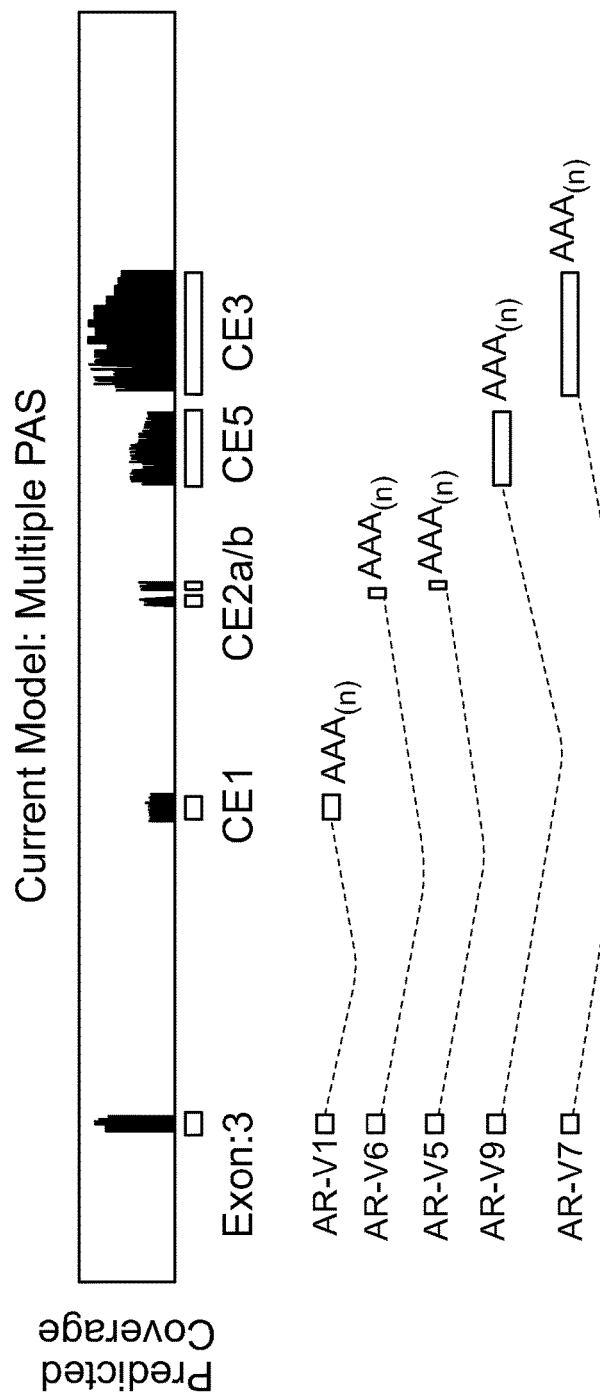
FIGS. 11A-11D show that blockade of the AR CE3 PAS inhibits AR-V expression.
Figure 11B:
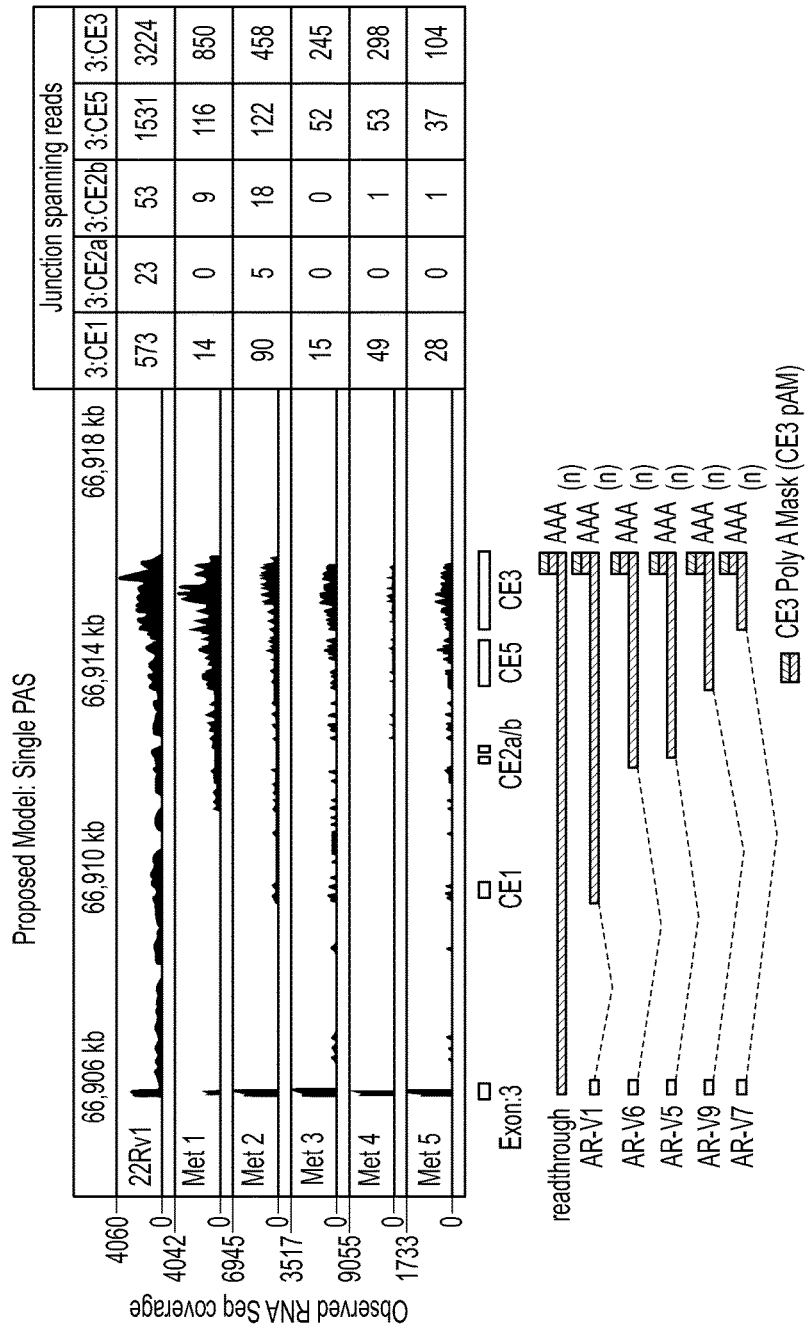

Having ruled out splice acceptor site recognition as a main mechanism, alternative polyadenylation was addressed. The current model for splicing of AR-V7 and other AR-Vs is that each cryptic exon in AR intron 3 harbors discrete splice acceptor and polyadenylation sites (PAS; Guo et al., 2009, *Cancer Res.*, 69:2305-13). This model would predict RNA-seq coverage beginning at each splice acceptor, and terminating at each PAS (FIG. 11A). However, when RNA-seq read coverage from 22Rv1 cells and CRPC metastases was analyzed, patterns that were inconsistent with this model were observed (FIG. 11B). For example, it was noted that signal attenuation at the 3' end of CE3 consistent with mRNA cleavage and polyadenylation, but lack of signal initiation at the CE3 splice acceptor site, despite abundant exon 3/CE3 splice junctions (FIG. 11B). Similarly, CE1, CE2, and CE5 also lacked distinct 5' and 3' termini, despite abundant exon 3/CE1, 3/CE2, and 3/CE5 splice junctions (FIG. 11B).

Figure 11C:
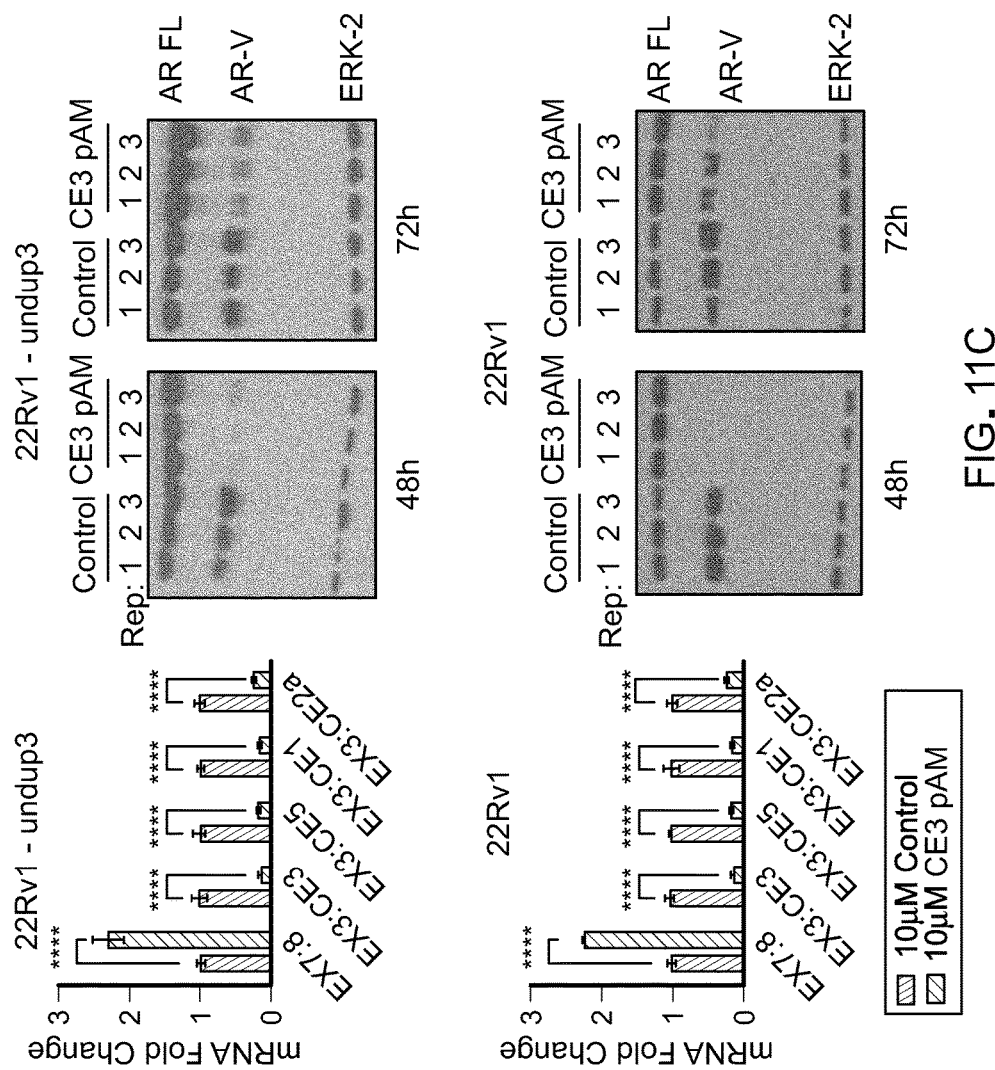
Figure 12A:
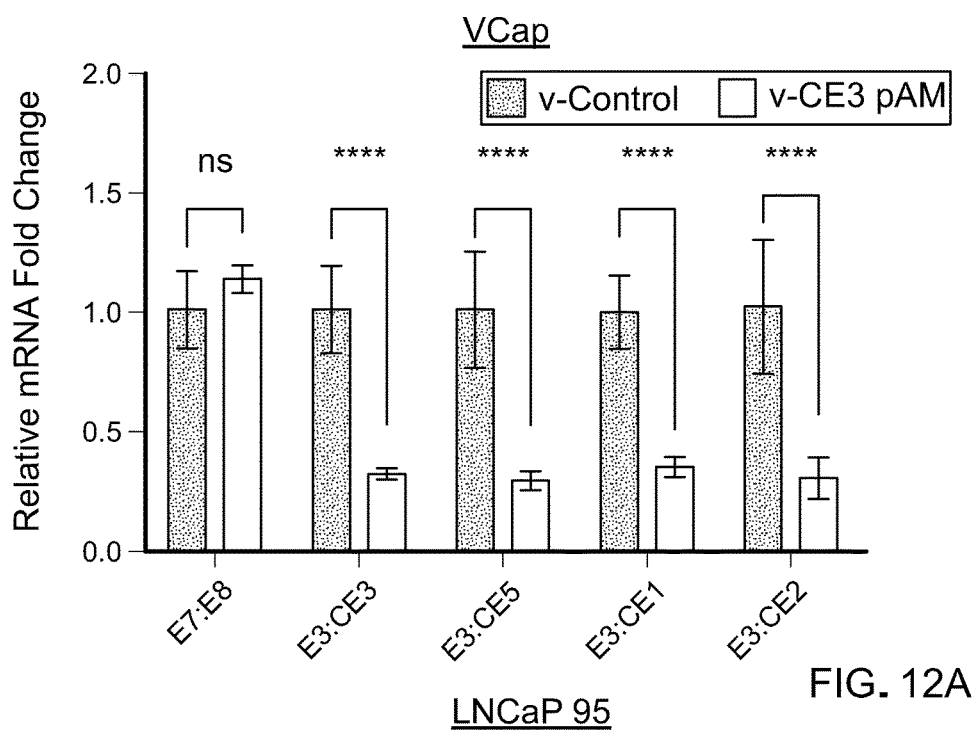
FIGS. 12A-12B contain graphs showing that blockade of the AR CE3 PAS blocks AR-V expression in VCaP cells (FIG. 12A) and in LNCaP 95 cells (FIG. 12B). Cells were incubated in the presence of 1 μM vivo-control morpholino (grey bars) or 1 μM vivo-CE3 pAM for 72 hours in androgen replete, reduced serum culture medium. Mean mRNA fold change of AR and AR-Vs relative to actin control from 3 biological replicates is shown (n=6, error bars=95% confidence intervals). **p≤0.0001, *p≤0.001, ns p≥0.05, unpaired t-tests.
Figure 12B:
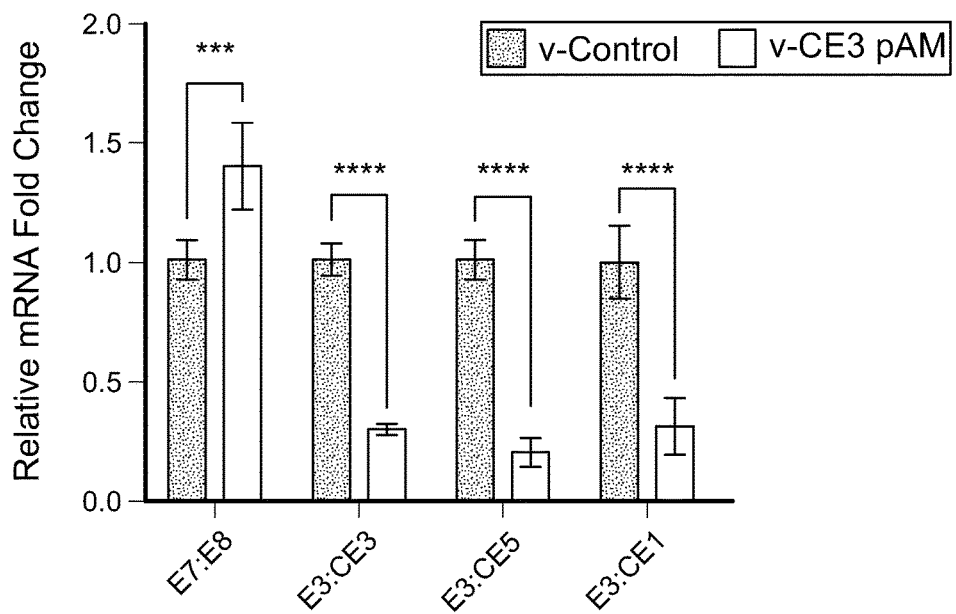
Figure 13A:
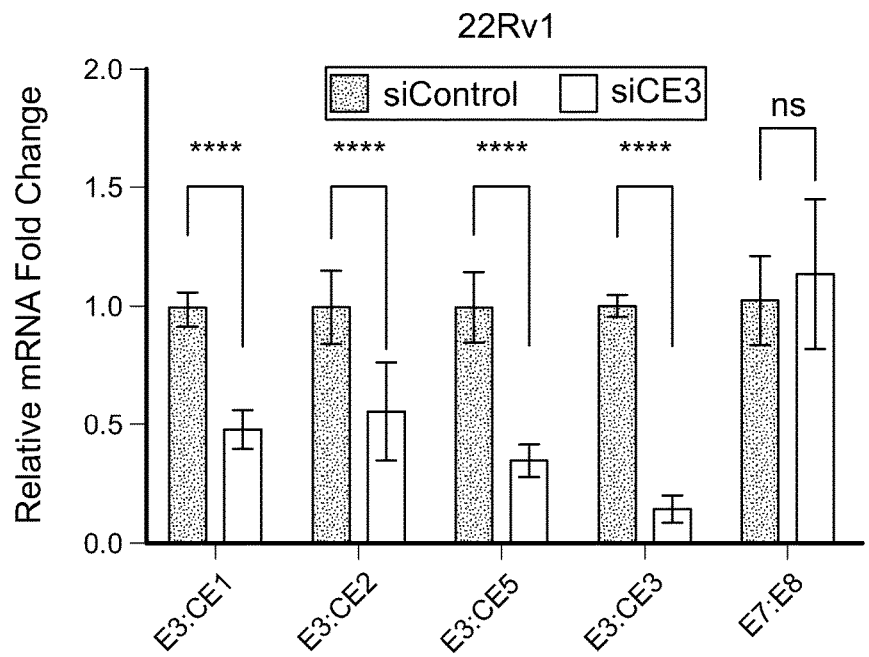
FIGS. 13A-13B contain graphs showing that knockdown of CE3 reduces relative levels of mRNAs harboring AR exon 3 spliced to CE1, CE2, and CE5 in 22Rv1 cells (FIG. 13A, n=4) and in VCaP cells (FIG. 13B, n=6). Bars represent mean mRNA fold changes relative to nontargeting control, error bars represent 95% confidence intervals. Asterisks indicate p values calculated by a two tailed t-test (p values; **p≤0.0001, *p≤0.001, **p≤0.01, *p≤0.05, ns p>0.05). Actin was used as an internal control (calibrator) for qPCR studies.
Figure 13B:
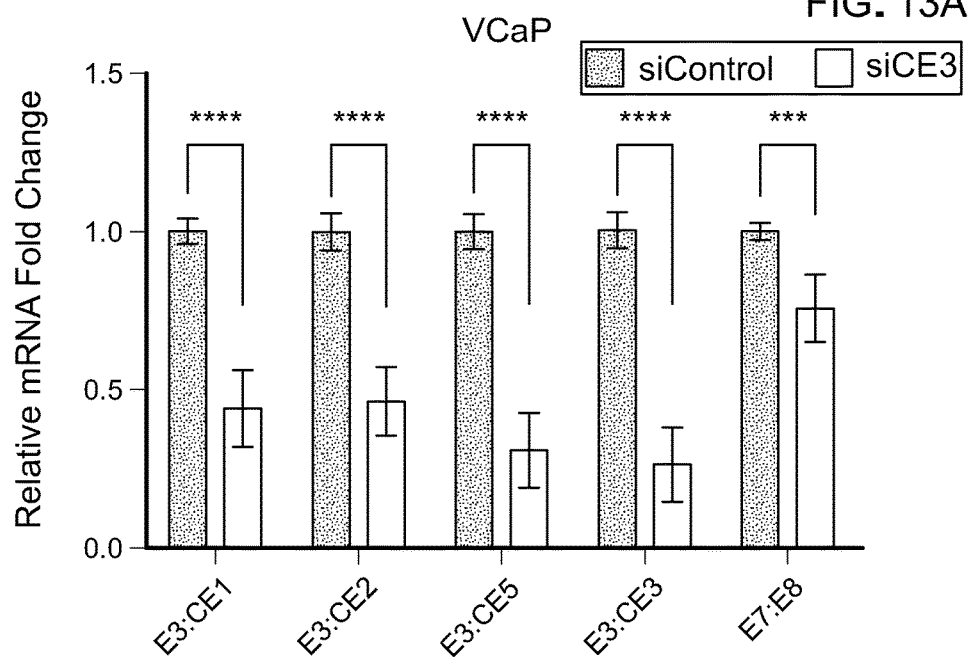

An alternative model was developed, where AR-V mRNAs would arise from the use of annotated splice acceptor sites within AR intron 3, but would all terminate at a single PAS that had been annotated previously for CE3 (FIG. 11B) (Guo et al., 2009, *Cancer Res.*, 69:2305-13). To test this model, a morpholino termed CE3 poly A mask (pAM) was designed to impose a steric blockade by hybridization to the CE3 PAS (FIG. 11B). Consistent with a single PAS model, 22Rv1 and 22Rv1-undup3 cells transfected with CE3 pAM displayed a reduction in mRNA and protein expression of AR-V7 as well as AR-V9 (EX3:CE5), AR-V1 (EX3:CE1), and AR-V6 (EX3:CE2a), accompanied by an increase in expression of AR-FL (FIG. 11C). A specific reduction of AR-V mRNAs in VCaP and LN95 cells treated with a vivo-morpholino targeting the same sequence as CE3 pAM was also observed, which indicates this effect was not restricted to the 22Rv1 genetic background (FIG. 12). In this alternative model, the entire cohort of AR-V mRNAs could be susceptible to knockdown with siRNA targeting AR exon CE3, which has been assumed to target AR-V7 specifically (Li et al., 2012, *Oncogene*, 31:4759-67; Li et al., 2013, *Cancer Res* 73:483-9; Guo et al., 2009, *Cancer Res.*, 69:2305-13; and Yu et al., 2014, *Clin. Cancer. Res.*, 20:1590-600). Indeed, transfection of 22Rv1 and VCaP cells with siRNAs targeted to AR exon CE3 resulted in knockdown of AR-V1, AR-V6, AR-V9, and AR-V7 mRNA expression (FIG. 13).

Figure 11D:
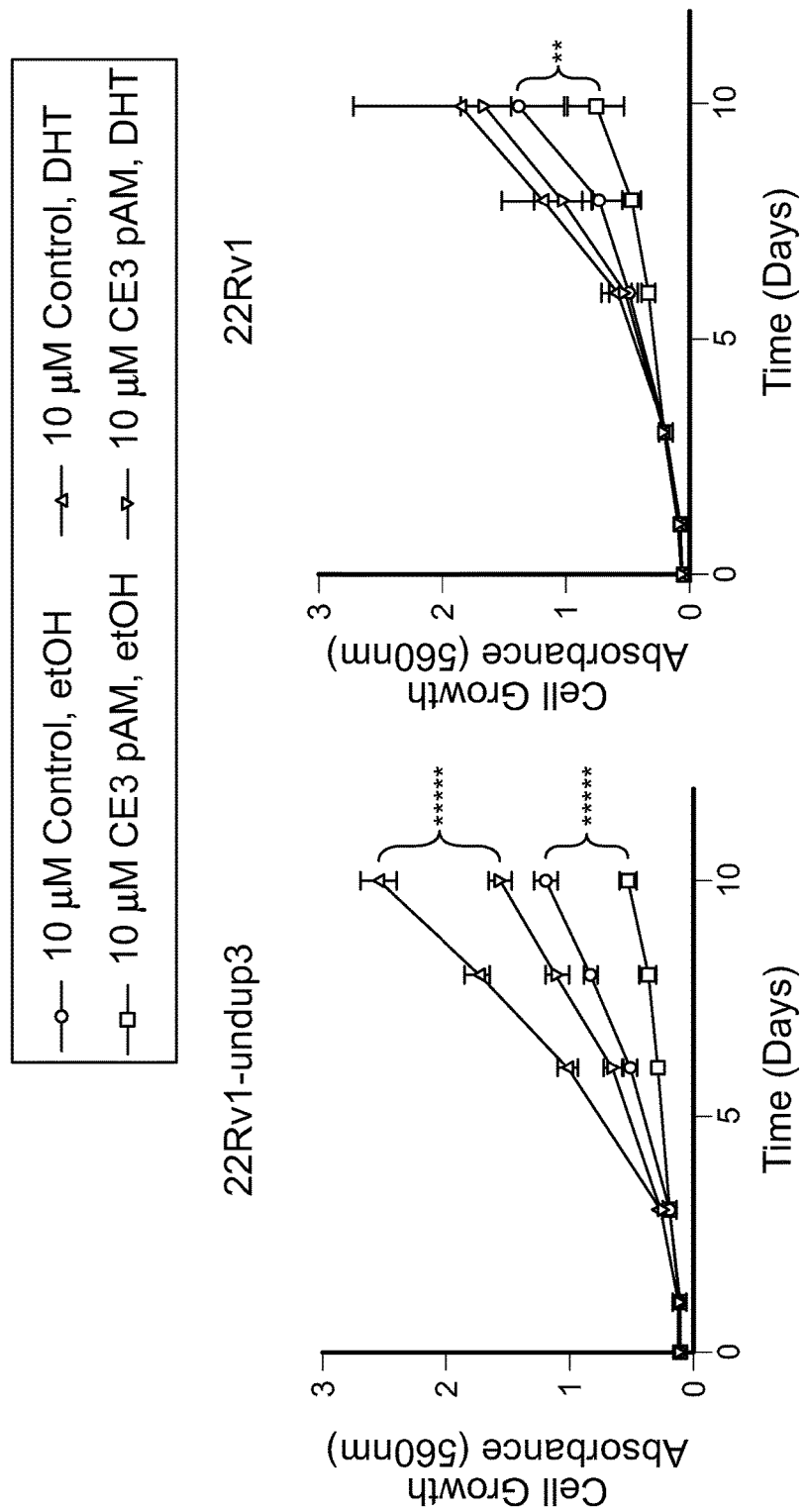

Since CE3-pAM reduced expression of multiple AR-Vs, whether CE3-pAM would inhibit growth of AR-V-positive prostate cancer cells under castrate conditions was examined. Indeed, a reduction in growth of 22Rv1-undup3 and parental 22Rv1 cells transfected with CE3-pAM under androgen-deplete conditions was observed (FIG. 11D). CE3-pAM also inhibited growth of 22Rv1-undup3 cells under androgen-replete conditions (FIG. 11D).

mRNA 3' End Processing Factors are Enriched in Prostate Cancer

Figure 14A:
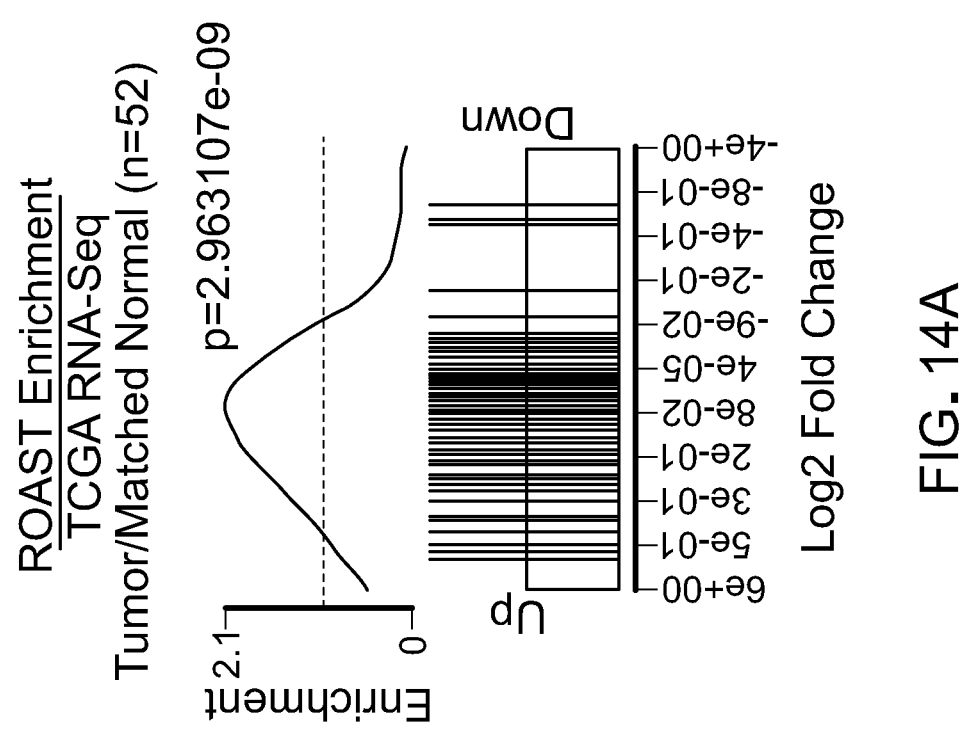
FIGS. 14A-14D show CPSF complex alterations in prostate cancer.
Figure 14B:
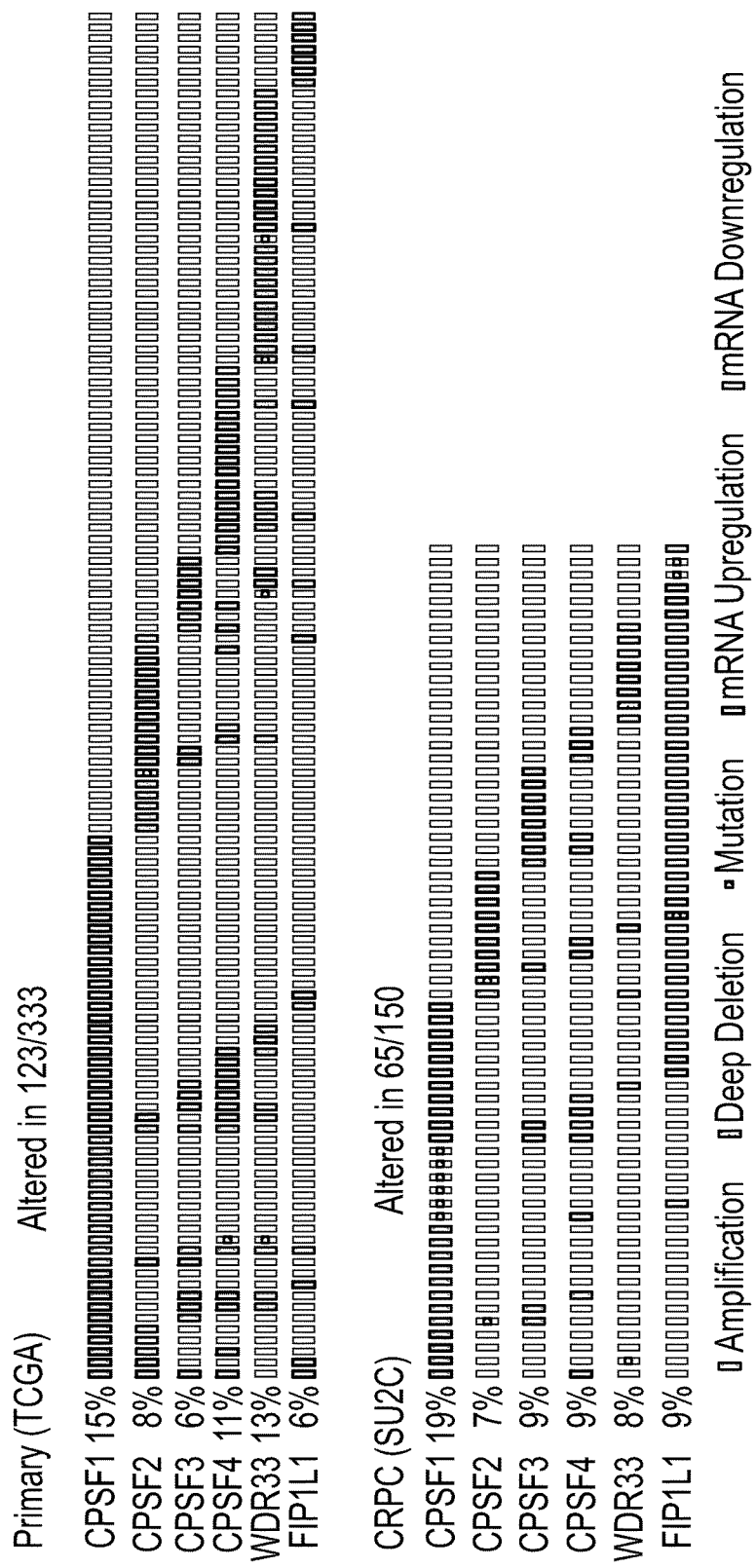
Figure 15:
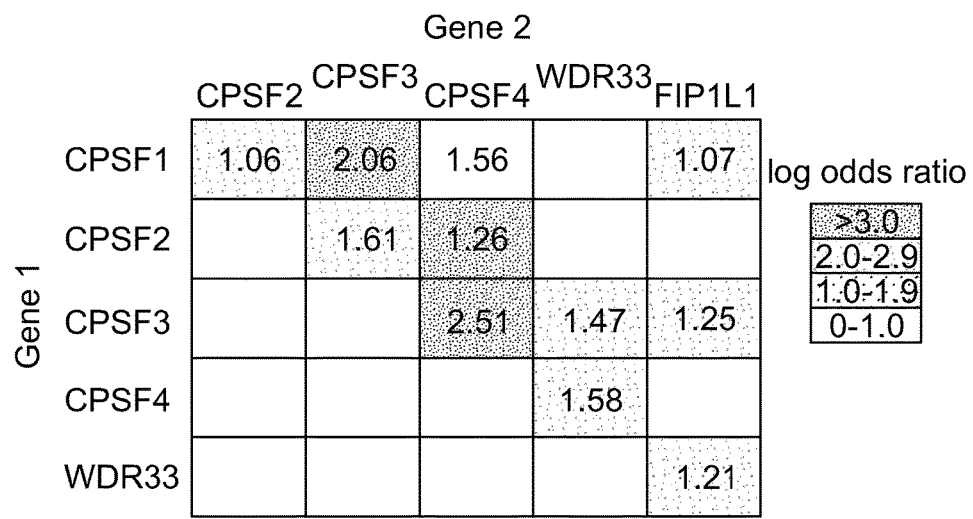
FIG. 15 shows a mutual exclusivity matrix depicting co-occurrence of alterations in the core CPSF complex. Analysis was performed in cBioPortal on TCGA whole genome and RNA-seq datasets. Positive log odds ratios from Fisher's exact test are depicted.

In view of the data pointing to regulation of AR-V expression by alternative polyadenylation, 52 pairs of normal and matched prostate cancer tissues were interrogated for altered expression of a set of 91 genes that encode factors involved in mRNA 3' end processing (Abeshouse et al., 2015, *Cell*, 163:1011-25; Shi et al., 2009, *Mol. Cell.*, 33:365-76; and Wu et al., 2010, *Bioinformatics*, 26:2176-82). Using rotation gene set tests (ROAST), these factors were found to be upregulated in tumor relative to matched normal tissues (FIG. 14A). Public datasets were queried for alterations in the 6 core genes encoding the cleavage and polyadenylation specificity factor (CPSF) complex: CPSF1, CPSF2, CPSF3, CPSF4, WDR33, and FIP1. Upon recruitment of this complex to pre-mRNAs, CPSF4 and WDR33 contact the PAS (Chan et al., 2014, *Genes Dev.*, 28:2370-80; and Schonemann et al., 2014, *Genes Dev.*, 28:2381-93) and CPSF3 cleaves mRNA downstream of the PAS, triggering polyadenylation (Ryan et al., 2004, *RNA*, 10:565-73). CPSF complex factors displayed alterations at the level of genomic copy number, gene mutation, and mRNA abundance, with CPSF1 displaying frequent alterations (FIG. 14B). Additionally, trends of co-occurring alterations in CPSF complex factors in localized prostate tumors were noted (FIG. 14B and FIG. 15).

Figure 14C:
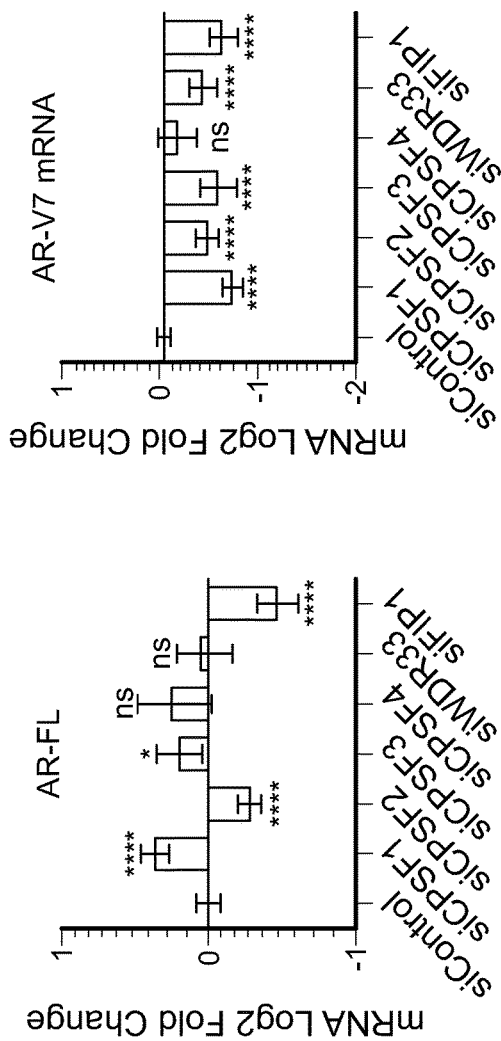
Figure 16:
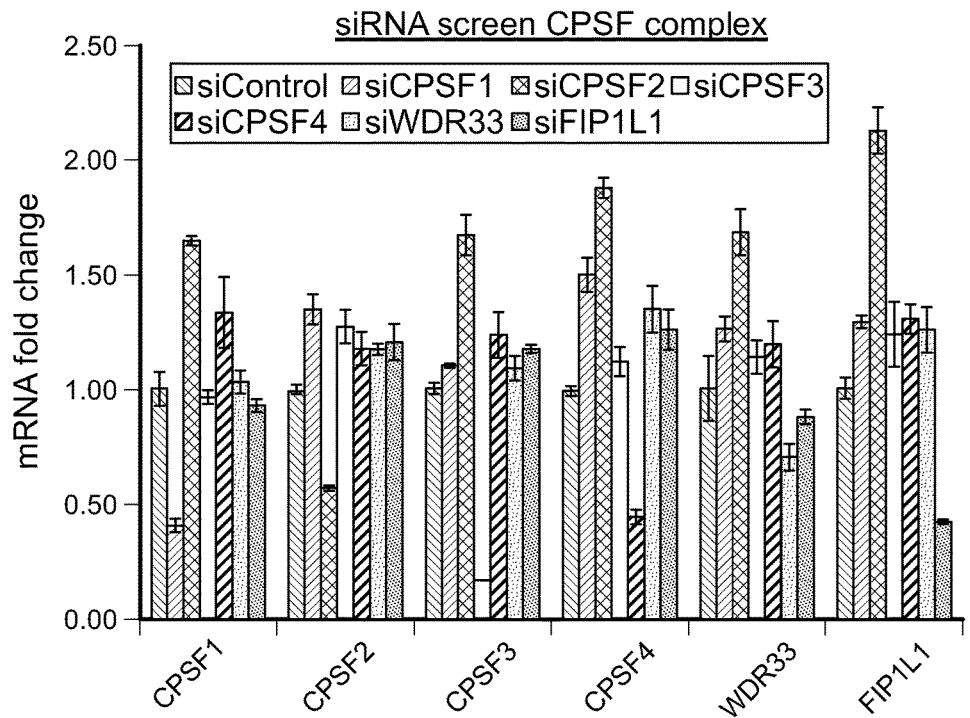
FIG. 16 shows an siRNA screen of the CPSF complex confirming CPSF complex gene knockdown. siRNA pools targeting each CPSF core complex gene were transfected into 22Rv1 cells. Knockdown was assessed at the mRNA level by RT-qPCR. The comparative ΔΔCt method was used to calculate mRNA fold changes relative to 18S rRNA. Bars represent mean mRNA fold change. Error bars indicate standard deviation, n=3.

To test the role of the CPSF complex in regulating AR splicing, a siRNA-based screen was performed, prioritizing factors that would cause an AR splicing switch when knocked-down, as opposed to general reductions in expression of both AR-V7 and AR-FL due to possible non-specific effects. Depletion of CPSF1 and CPSF3 led to reduced expression of AR-V7 and increased expression of AR-FL mRNA in 22Rv1-undup3 cells (FIG. 14C and FIG. 16). These effects were similar to the splice switch observed in cells treated with CE3-pAM (FIG. 11C).

Figure 14D:
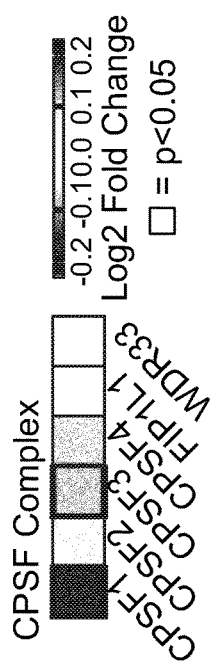

Next, publicly available RNA-seq data were analyzed for evidence of alterations in CPSF1 or CPSF3 expression. It was observed that CPSF1 and CPSF3 mRNA levels were upregulated in primary prostate cancer vs. matched normal prostate tissue (FIG. 14D). Since CPSF1 was frequently altered in prostate cancer tissues (FIG. 14B), and had the most robust effect on AR splice switching (FIG. 14C), CPSF1 was further analyzed.

Figure 17:
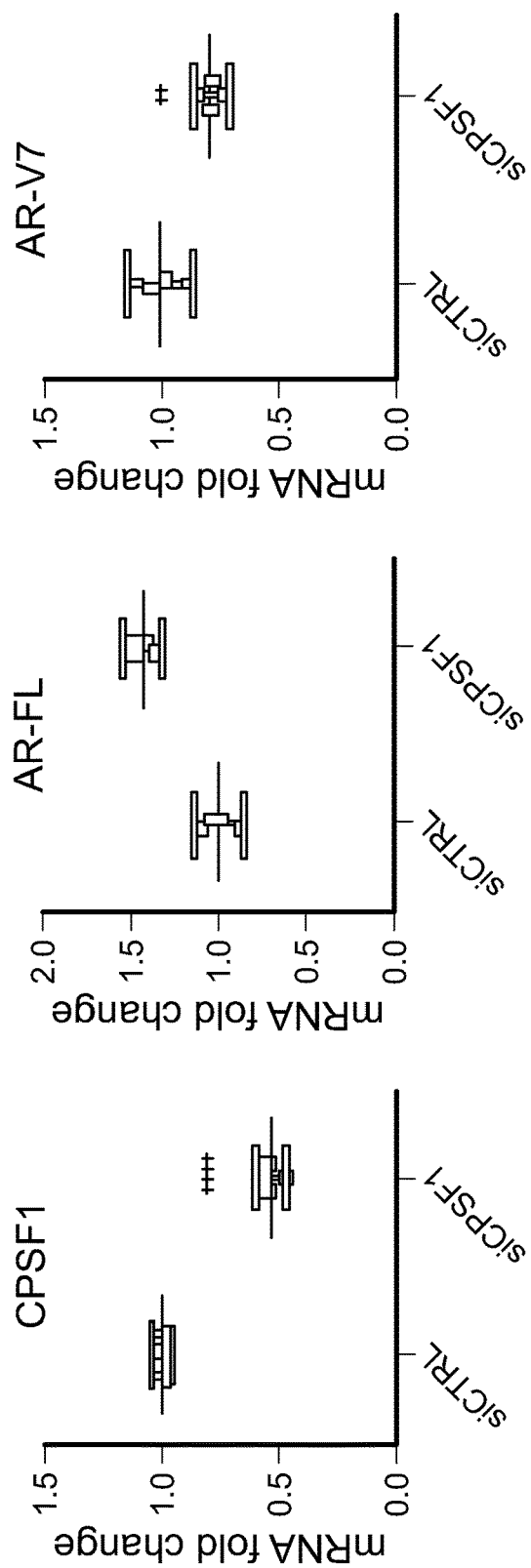
FIG. 17 contains graphs of relative mRNA levels of AR and AR-V7 after knockdown of CPSF1 in LNCaP 95 cells (siControl: nontargeting siRNA, siCPSF1: CPSF1 smartpool). Relative mRNA fold change from 2 biological and 2 technical replicates are plotted (n=4); the center line represents the mean; error bars represent 95% confidence intervals. 18S served as an internal control. **p≤0.0001, *p≤0.001, **p≤0.01, unpaired t-tests.
Figure 18A:
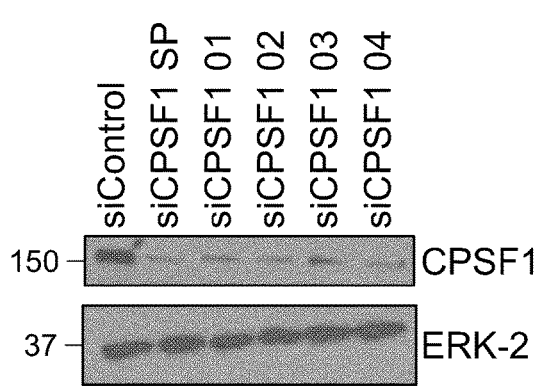
FIGS. 18A-18C show that CPSF1 regulates AR-V expression.
Figure 18B:
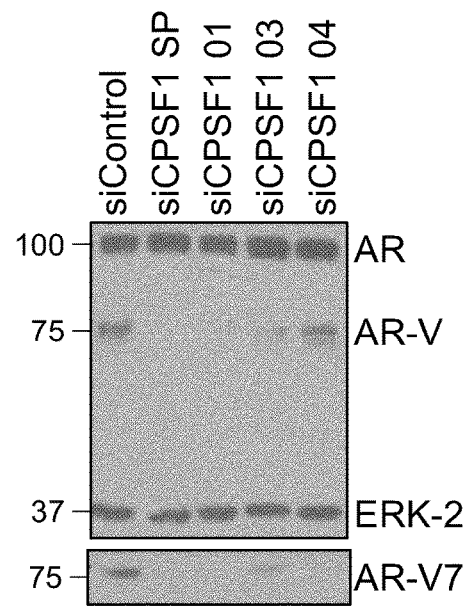
Figure 18C:
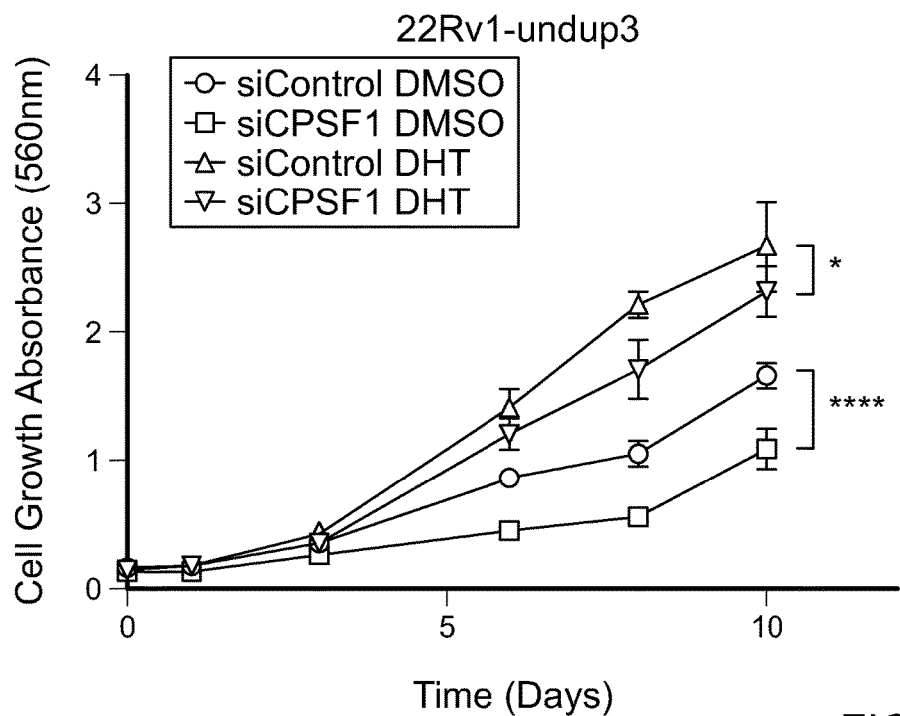

CPSF1 was knocked down in LNCaP-95 cells, which confirmed the increase in AR-FL and decrease in AR-V7 mRNA expression was not restricted to the 22Rv1 genetic background (FIG. 17A). Next, CPSF1 was knocked down in 22Rv1-undup3 cells using four CPSF1 siRNAs delivered individually or as a pool (FIG. 18A). One of these reagents (siCPSF 02) was omitted from further study due to toxicity. Knock-down of CPSF1 reduced expression of AR-V7 protein and increased expression of AR-FL protein (FIG. 18B). Accordingly, knock-down of CPSF1 with three independent siRNAs resulted in reduced growth of 22Rv1-undup3 cells under androgen deplete conditions (FIG. 18C). Under androgen-replete conditions, CPSF1 knockdown had a modest effect on 22Rv1-undup3 cell growth, which could be attributed to general effects on mRNA processing by CPSF1 knockdown (FIG. 18C).

Figure 18D:
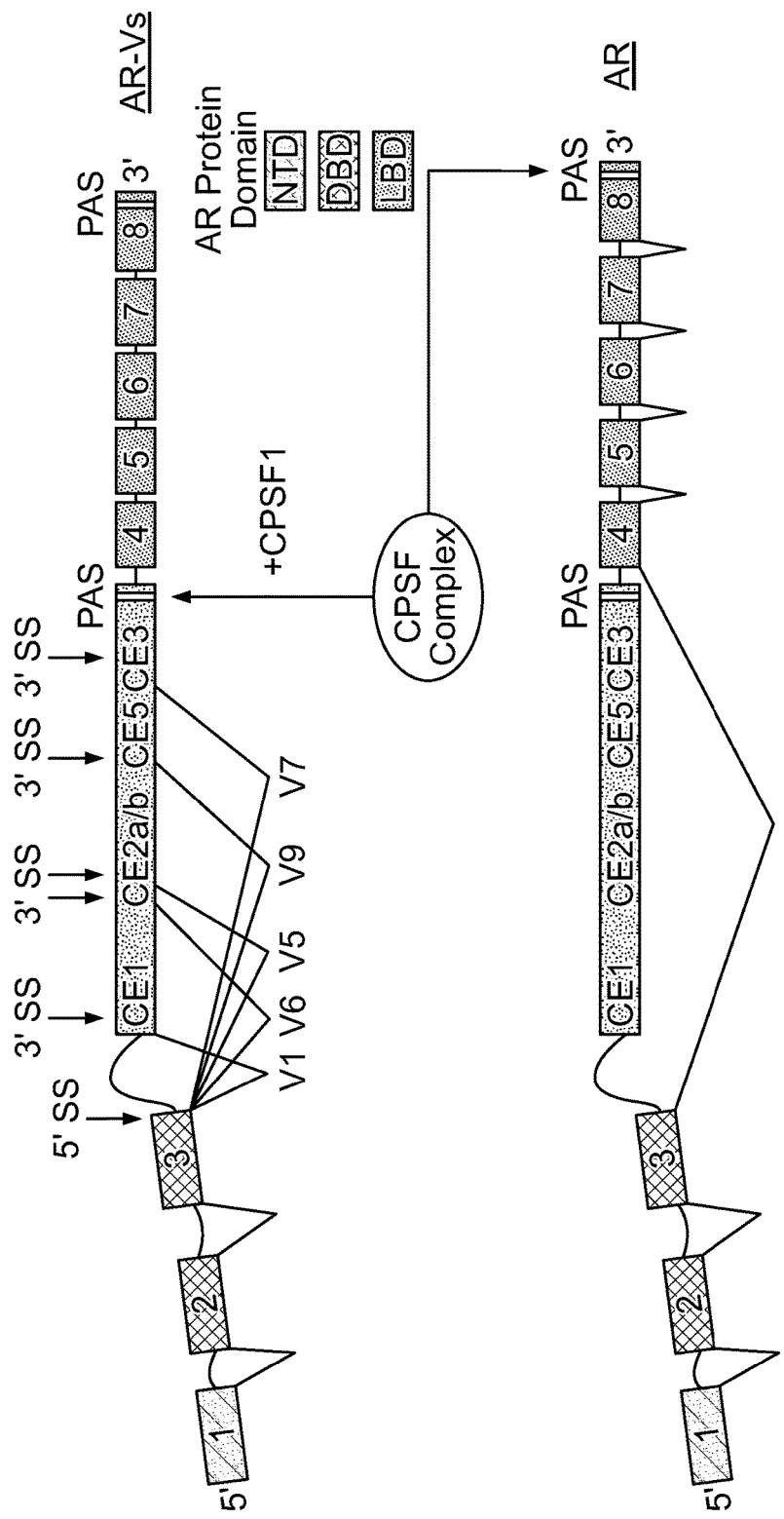

Collectively, these data re-annotate AR CE1, CE2, CE5, and CE3 as harboring independent splice acceptor sites but sharing a single PAS that was previously thought to be used exclusively for synthesis of AR-V7. This PAS appears to be the main regulatory point for all AR-Vs utilizing cryptic exons in AR intron 3, as alternative PASs did not appear to become activated following morpholino blockade of the CE3 PAS. These data support a model whereby alterations in CPSF1 expression and/or activity promote selection of the intronic AR CE3 PAS, leading to recruitment of the CPSF complex to drive synthesis of multiple AR-V mRNAs, including AR-V7 (FIG. 18D).

Together these results demonstrate that inhibiting expression of AR-Vs including AR-V7 (e.g., using an AR-V inhibitor) can overcome therapeutic resistance in prostate cancer (e.g., can be used to treat CRPC).

Example 3

Targeting a Single Alternative Polyadenylation Site to Coordinately Block Expression of Androgen Receptor mRNA Splice Variants In Vivo Materials and Methods
Morpholino Transfections GeneTools' design tool was used to design morpholinos targeting upstream and downstream regions of AR CE3. Sequences were as follows:

```
us 100-
                                    (SEQ ID NO: 62)
5'-ACCTCATTAGCCTTTCAATCCACAT-3', us 50-
                                    (SEQ ID NO: 63)
5'-CACTAGTAGAAATATGCAACATTCA-3', ds 50-
                                    (SEQ ID NO: 64)
5'-AGCATTAATTCTCTCAGTCTGTTGT-3', ds 150-
                                    (SEQ ID NO: 65)
5'-AGCATGACCTGGAAAGCAAACGAGA-3'.
```

22Rv1 cells were transfected with 10 µM control and morpholinos tiling upstream (us) and downstream (ds) of the CE3 PAS (us 100, us 50, CE3 pAM, ds 50, ds 150).

Xenograft Models

Mouse strains used in this study were athymic nu/nu/Foxn1nu homozygote male mice, aged 6-7 week (obtained from Envigo). Tumors were established by injecting $1 \times 10^6$ cells in a final volume of 0.05 mL in cell culture medium mixed with 0.05 mL matrigel subcutaneously into left and right flanks of mice. When tumors reached 100 mm$^3$, 0.2 mg control vivo-morpholino or CE3-pAM vivo-morpholino in 1×PBS in a final volume of 0.05 mL was injected directly into tumors. Four mice were used per group. Drug injections were repeated every three days for a total of three injections. Mice were euthanized 24 hours after the last injection. Tumors were resected and snap frozen in liquid nitrogen for later processing.

RNA Purification from Tumor Tissue

Total RNA from tumor tissue was purified using the Promega Reliaprep Tissue kit according to manufacturer instructions, including the on-column DNAse treatment. RNA was eluted in nuclease free water. Reverse transcription and quantitative PCR were performed as described in Example 2. Data were analyzed using the ΔΔCt method and normalized to actin-2 (internal control).

Results

CE3 pAM is Specific for the Polyadenylation Signal in AR CE3

To test the specificity of CE3 pAM for the polyadenylation signal (PAS) in AR CE3, four morpholinos were designed that target sequences flanking the CE3 PAS. These flanking morpholinos bind with high affinity to regions roughly 50 and 100 base pairs upstream and 50 and 150 base pairs downstream of the PAS in CE3 (FIG. 19A). To test whether steric blockade of sequences flanking the AR CE3 PAS would impact AR-V7 expression, 22Rv1 cells were transfected with 10 µM control and morpholinos tiling these regions and the impact of each morpholino on AR and AR-V7 mRNA levels was measured. Transfection of CE3 pAM reduced AR-V7 mRNA and increased AR mRNA, whereas morpholinos tiling upstream and downstream sequences in CE3 conferred minimal effects on AR-V7 and AR mRNA levels (FIG. 19B). Similar results were seen for AR-V7 and AR protein levels (FIG. 19C). These data showed that CE3 pAM reduced AR-V7 mRNA levels via interaction with the CE3 PAS. Furthermore, they indicated that steric blockade of the CE3 pAM sequence is sufficient to block expression of AR-V7 and other AR-V mRNAs.

Xenograft Model

Whether the molecular effects of CE3 pAM in vitro could be extended to tumor xenograft models in mice was tested. Tumors were established in intact athymic nu/nu/Foxn1nu homozygote male mice by injecting $1 \times 10^6$ 22 Rv1 cells subcutaneously in left and right flanks. When tumors reached 100 mm$^3$, 0.2 mg control vivo-morpholino or 0.2 mg CE3 pAM vivo-morpholino was injected directly into tumors. Injections were repeated on days 1, 4, and 7 of the study. A reduction in AR-V7 mRNA levels in tumor tissues treated with CE3 pAM relative to controls (FIG. 20; *$p \leq 0.05$ in two-tailed t test). All statistics were performed in GraphPad.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. An androgen receptor variant (AR-V) inhibitor oligonucleotide, wherein said AR-V inhibitor oligonucleotide comprises:

an antisense sequence about 22 nucleotides to about 200 nucleotides in length which is complementary to a target sequence in cryptic exon 3 of an AR transcript, wherein said antisense sequence comprises at least one modified nucleotide, wherein said antisense sequence has at least 90 percent sequence identity to SEQ ID NO:2, and wherein said antisense sequence comprises SEQ ID NO:1; and wherein said AR-V inhibitor oligonucleotide binds to the AR transcript and inhibits expression of one or more AR-Vs.

2. The AR-V inhibitor oligonucleotide of claim 1, wherein said antisense sequence is about 22 to about 30 nucleotides in length.

3. The AR-V inhibitor oligonucleotide of claim 1, wherein said antisense sequence comprises SEQ ID NO:2.

4. The AR-V inhibitor oligonucleotide of claim 1, wherein said target sequence comprises a polyadenylation site.

5. The AR-V inhibitor oligonucleotide of claim 1, wherein said target sequence comprises SEQ ID NO:3.

6. The AR-V inhibitor oligonucleotide of claim 5, wherein said target sequence comprises SEQ ID NO:4.

7. The AR-V inhibitor oligonucleotide of claim 1, wherein said one or more AR-Vs are selected from the group consisting of AR-V2, AR-V5, AR-V7, and/or AR-V9.

8. The AR-V inhibitor oligonucleotide of claim 7, wherein said AR-V inhibitor oligonucleotide inhibits expression of AR-V7.

9. The AR-V inhibitor oligonucleotide of claim 1, wherein said AR-V inhibitor oligonucleotide is conjugated to a cell-penetrating peptide.

10. The AR-V inhibitor oligonucleotide of claim 9, wherein said cell-penetrating peptide comprises an 8 guanidine head group.

11. The AR-V inhibitor oligonucleotide of claim 1, wherein said at least one modified nucleotide comprises a morpholine ring.

12. The AR-V inhibitor oligonucleotide of claim 1, wherein said at least one modified nucleotide comprises a phosphorodiamidate linkage.

13. The AR-V inhibitor oligonucleotide of claim 1, wherein said AR-V inhibitor oligonucleotide is a morpholino.

14. A method for treating castration-resistant prostate cancer (CRPC) in a mammal, the method comprising:
identifying said mammal as having a CRPC expressing one or more androgen receptor variants (AR-Vs); and
administering to said mammal an AR-V inhibitor oligonucleotide, wherein said AR-V inhibitor oligonucleotide comprises an antisense sequence about 22 nucleotides to about 200 nucleotides in length which is complementary to a target sequence in cryptic exon 3 of an AR transcript, wherein said antisense sequence comprises at least one modified nucleotide, wherein said antisense sequence has at least 90 percent sequence identity to SEQ ID NO:2, and wherein said antisense sequence comprises SEQ ID NO:1;
wherein said AR-V inhibitor oligonucleotide binds to the AR transcript and inhibits expression of one or more AR-Vs.

15. The method of claim 14, wherein said mammal is a human.

16. The method of claim 14, wherein said one or more AR-Vs are selected from the group consisting of AR-V2, AR-V5, AR-V7, and/or AR-V9.

17. The method of claim 16, wherein said AR-V inhibitor oligonucleotide inhibits expression of AR-V7.

18. The method of claim 14, wherein said AR-V inhibitor oligonucleotide restores androgen responsiveness to a CRPC.

19. The method of claim 14, wherein said antisense sequence comprises SEQ ID NO:2.

20. The method of claim 14, wherein said target comprises a polyadenylation site.

21. The method of claim 14, wherein said target sequence comprises SEQ ID NO:3.

22. The method of claim 21, wherein said target sequence comprises SEQ ID NO:4.

23. The method of claim 14, wherein said AR-V inhibitor oligonucleotide is a morpholino.

24. The method of claim 23, wherein said additional cancer treatment comprises androgen deprivation therapy.

25. The method of claim 24, wherein said androgen deprivation therapy comprises administering an antiandrogen.

* * * * *

SEQUENCE LISTING

<160> NUMBER OF SEQ ID NOS: 65

<210> SEQ ID NO 1
<211> LENGTH: 6
<212> TYPE: DNA
<213> ORGANISM: Artificial

-continued

```
<220> FEATURE:
<223> OTHER INFORMATION: antisense sequence complementary to a non-
      canonical polyadenylation site in cryptic exon 3

<400> SEQUENCE: 1 tttatt                                                                      6

<210> SEQ ID NO 2
<211> LENGTH: 25
<212> TYPE: DNA
<213> ORGANISM: Artificial
<220> FEATURE:
<223> OTHER INFORMATION: CE3 pAM morpholino

<400> SEQUENCE: 2
gtgtattaat ggctttatta aggga                                                25

<210> SEQ ID NO 3
<211> LENGTH: 6
<212> TYPE: RNA
<213> ORGANISM: Homo sapiens

<400> SEQUENCE: 3 aauaaa                                                                      6

<210> SEQ ID NO 4
<211> LENGTH: 25
<212> TYPE: RNA
<213> ORGANISM: Homo sapiens

<400> SEQUENCE: 4
ucccuuaaua aagccauuaa uacac                                                25

<210> SEQ ID NO 5
<211> LENGTH: 50
<212> TYPE: DNA
<213> ORGANISM: Artificial
<220> FEATURE:
<223> OTHER INFORMATION: 3' breakpoint sequence junction of 22Rv1 sub-
      line undup3

<400> SEQUENCE: 5
tatataacaa tttcagagag tccacggact ctctgaaatt gttataaggt                     50

<210> SEQ ID NO 6
<211> LENGTH: 50
<212> TYPE: DNA
<213> ORGANISM: Artificial
<220> FEATURE:
<223> OTHER INFORMATION: 3' breakpoint sequence junction of 22Rv1 sub-
      line undup2

<400> SEQUENCE: 6
ataacaattt cagagagtcc acatattgtt ataaggtctt tttctttgtt                     50

<210> SEQ ID NO 7
<211> LENGTH: 50
<212> TYPE: DNA
<213> ORGANISM: Artificial
<220> FEATURE:
<223> OTHER INFORMATION: 3' breakpoint sequence junction of 22Rv1 sub-
      line undup1

<400> SEQUENCE: 7
tatataacaa tttcagagag tccacggact ctctgaaatt gttataaggt                     50
```

-continued

```
<210> SEQ ID NO 8
<211> LENGTH: 50
<212> TYPE: DNA
<213> ORGANISM: Artificial
<220> FEATURE:
<223> OTHER INFORMATION: 5' breakpoint sequence junction of 22Rv1 sub-
      line undup3

<400> SEQUENCE: 8
atgaacattc ctgcctggct gacatcttta ctcatatata ctttagattc          50

<210> SEQ ID NO 9
<211> LENGTH: 50
<212> TYPE: DNA
<213> ORGANISM: Artificial
<220> FEATURE:
<223> OTHER INFORMATION: 5' breakpoint sequence junction of 22Rv1 sub-
      line undup2

<400> SEQUENCE: 9
ggatgaacat tcctgcctgg ctgacggtgg cggcaagcaa gcgctcgaaa          50

<210> SEQ ID NO 10
<211> LENGTH: 50
<212> TYPE: DNA
<213> ORGANISM: Artificial
<220> FEATURE:
<223> OTHER INFORMATION: 5' breakpoint sequence junction of 22Rv1 sub-
      line undup1

<400> SEQUENCE: 10
atgaacattc ctgcctggct gacatcttta ctcatatata ctttagattc          50

<210> SEQ ID NO 11
<211> LENGTH: 32
<212> TYPE: DNA
<213> ORGANISM: Artificial
<220> FEATURE:
<223> OTHER INFORMATION: synthetic primer

<400> SEQUENCE: 11
ctcccaacaa gtgatcagta gtcagaaaat gg                            32

<210> SEQ ID NO 12
<211> LENGTH: 33
<212> TYPE: DNA
<213> ORGANISM: Artificial
<220> FEATURE:
<223> OTHER INFORMATION: synthetic primer

<400> SEQUENCE: 12
caacagggta tcttattttg caaaccctaa gtc                           33

<210> SEQ ID NO 13
<211> LENGTH: 19
<212> TYPE: RNA
<213> ORGANISM: Artificial
<220> FEATURE:
<223> OTHER INFORMATION: siRNA targeting AR CE3

<400> SEQUENCE: 13
guaguuguga guaucauga                                           19

<210> SEQ ID NO 14
<211> LENGTH: 21
<212> TYPE: RNA
<213> ORGANISM: Artificial
```

```
<220> FEATURE:
<223> OTHER INFORMATION: siRNA targeting AR CE3

<400> SEQUENCE: 14
aggacgggcu guagaaguau u                                              21

<210> SEQ ID NO 15
<211> LENGTH: 21
<212> TYPE: RNA
<213> ORGANISM: Artificial
<220> FEATURE:
<223> OTHER INFORMATION: siRNA targeting AR CE3

<400> SEQUENCE: 15
uacuucuaca gcccguccuu u                                              21

<210> SEQ ID NO 16
<211> LENGTH: 21
<212> TYPE: RNA
<213> ORGANISM: Artificial
<220> FEATURE:
<223> OTHER INFORMATION: siRNA targeting AR CE3

<400> SEQUENCE: 16
caaaaugacc agacccugau u                                              21

<210> SEQ ID NO 17
<211> LENGTH: 21
<212> TYPE: RNA
<213> ORGANISM: Artificial
<220> FEATURE:
<223> OTHER INFORMATION: siRNA targeting AR CE3

<400> SEQUENCE: 17
ucagggucug gucauuuugu u                                              21

<210> SEQ ID NO 18
<211> LENGTH: 19
<212> TYPE: DNA
<213> ORGANISM: Artificial
<220> FEATURE:
<223> OTHER INFORMATION: synthetic primer

<400> SEQUENCE: 18
gaaggtgaag gtcggagtc                                                 19

<210> SEQ ID NO 19
<211> LENGTH: 20
<212> TYPE: DNA
<213> ORGANISM: Artificial
<220> FEATURE:
<223> OTHER INFORMATION: synthetic primer

<400> SEQUENCE: 19
gaagatggtg atgggatttc                                                20

<210> SEQ ID NO 20
<211> LENGTH: 20
<212> TYPE: DNA
<213> ORGANISM: Artificial
<220> FEATURE:
<223> OTHER INFORMATION: synthetic primer

<400> SEQUENCE: 20
aggccttccc tgtacaccaa                                                20
```

```
<210> SEQ ID NO 21
<211> LENGTH: 20
<212> TYPE: DNA
<213> ORGANISM: Artificial
<220> FEATURE:
<223> OTHER INFORMATION: synthetic primer

<400> SEQUENCE: 21
gtcttggcct ggtcatttcc                                              20

<210> SEQ ID NO 22
<211> LENGTH: 20
<212> TYPE: DNA
<213> ORGANISM: Artificial
<220> FEATURE:
<223> OTHER INFORMATION: synthetic primer

<400> SEQUENCE: 22
ctgccaaggt gcttctcatt                                              20

<210> SEQ ID NO 23
<211> LENGTH: 20
<212> TYPE: DNA
<213> ORGANISM: Artificial
<220> FEATURE:
<223> OTHER INFORMATION: synthetic primer

<400> SEQUENCE: 23
ctgtcaccct ggcaagaatc                                              20

<210> SEQ ID NO 24
<211> LENGTH: 20
<212> TYPE: DNA
<213> ORGANISM: Artificial
<220> FEATURE:
<223> OTHER INFORMATION: synthetic primer

<400> SEQUENCE: 24
aggagggaag agtcccagtg                                              20

<210> SEQ ID NO 25
<211> LENGTH: 20
<212> TYPE: DNA
<213> ORGANISM: Artificial
<220> FEATURE:
<223> OTHER INFORMATION: synthetic primer

<400> SEQUENCE: 25
tgggaagcta ctggttttgc                                              20

<210> SEQ ID NO 26
<211> LENGTH: 20
<212> TYPE: DNA
<213> ORGANISM: Artificial
<220> FEATURE:
<223> OTHER INFORMATION: synthetic primer

<400> SEQUENCE: 26
ctgtcagagc ctgccaagat                                              20

<210> SEQ ID NO 27
<211> LENGTH: 20
<212> TYPE: DNA
<213> ORGANISM: Artificial
<220> FEATURE:
<223> OTHER INFORMATION: synthetic primer
```

```
<400> SEQUENCE: 27
gcaagaactc ctctggttcg                                               20

<210> SEQ ID NO 28
<211> LENGTH: 20
<212> TYPE: DNA
<213> ORGANISM: Artificial
<220> FEATURE:
<223> OTHER INFORMATION: synthetic primer

<400> SEQUENCE: 28
tggatggata gctactccgg                                               20

<210> SEQ ID NO 29
<211> LENGTH: 20
<212> TYPE: DNA
<213> ORGANISM: Artificial
<220> FEATURE:
<223> OTHER INFORMATION: synthetic primer

<400> SEQUENCE: 29
cccagaagct tcatctccac                                               20

<210> SEQ ID NO 30
<211> LENGTH: 20
<212> TYPE: DNA
<213> ORGANISM: Artificial
<220> FEATURE:
<223> OTHER INFORMATION: synthetic primer

<400> SEQUENCE: 30
aacagaagta cctgtgcgcc                                               20

<210> SEQ ID NO 31
<211> LENGTH: 20
<212> TYPE: DNA
<213> ORGANISM: Artificial
<220> FEATURE:
<223> OTHER INFORMATION: synthetic primer

<400> SEQUENCE: 31
tcagggtctg gtcattttga                                               20

<210> SEQ ID NO 32
<211> LENGTH: 20
<212> TYPE: DNA
<213> ORGANISM: Artificial
<220> FEATURE:
<223> OTHER INFORMATION: synthetic primer

<400> SEQUENCE: 32
gaaactgcct caatccgggt                                               20

<210> SEQ ID NO 33
<211> LENGTH: 20
<212> TYPE: DNA
<213> ORGANISM: Artificial
<220> FEATURE:
<223> OTHER INFORMATION: synthetic primer

<400> SEQUENCE: 33
gtaactgcga ctcctgctgt                                               20
```

```
<210> SEQ ID NO 34
<211> LENGTH: 19
<212> TYPE: DNA
<213> ORGANISM: Artificial
<220> FEATURE:
<223> OTHER INFORMATION: synthetic primer

<400> SEQUENCE: 34
caggcctcac gactaccag                                                    19

<210> SEQ ID NO 35
<211> LENGTH: 19
<212> TYPE: DNA
<213> ORGANISM: Artificial
<220> FEATURE:
<223> OTHER INFORMATION: synthetic primer

<400> SEQUENCE: 35
gggaccacag tggacacaa                                                    19

<210> SEQ ID NO 36
<211> LENGTH: 20
<212> TYPE: DNA
<213> ORGANISM: Artificial
<220> FEATURE:
<223> OTHER INFORMATION: synthetic primer

<400> SEQUENCE: 36
cggggatctg acgagctttt                                                   20

<210> SEQ ID NO 37
<211> LENGTH: 20
<212> TYPE: DNA
<213> ORGANISM: Artificial
<220> FEATURE:
<223> OTHER INFORMATION: synthetic primer

<400> SEQUENCE: 37
tcggctgtca cctttgaact                                                   20

<210> SEQ ID NO 38
<211> LENGTH: 20
<212> TYPE: DNA
<213> ORGANISM: Artificial
<220> FEATURE:
<223> OTHER INFORMATION: synthetic primer

<400> SEQUENCE: 38
tgagactcca aacaccctca                                                   20

<210> SEQ ID NO 39
<211> LENGTH: 20
<212> TYPE: DNA
<213> ORGANISM: Artificial
<220> FEATURE:
<223> OTHER INFORMATION: synthetic primer

<400> SEQUENCE: 39
tatgacactc tgctgcctgc                                                   20

<210> SEQ ID NO 40
<211> LENGTH: 22
<212> TYPE: DNA
<213> ORGANISM: Artificial
<220> FEATURE:
<223> OTHER INFORMATION: synthetic primer
```

<400> SEQUENCE: 40
gcaaatgtct ccaaaaagca gc                                    22

<210> SEQ ID NO 41
<211> LENGTH: 28
<212> TYPE: DNA
<213> ORGANISM: Artificial
<220> FEATURE:
<223> OTHER INFORMATION: synthetic primer

<400> SEQUENCE: 41
cggaaatgtt atgaagcagg gatgactc                              28

<210> SEQ ID NO 42
<211> LENGTH: 24
<212> TYPE: DNA
<213> ORGANISM: Artificial
<220> FEATURE:
<223> OTHER INFORMATION: synthetic primer

<400> SEQUENCE: 42
ccagactatc cactagagcc ctct                                  24

<210> SEQ ID NO 43
<211> LENGTH: 21
<212> TYPE: DNA
<213> ORGANISM: Artificial
<220> FEATURE:
<223> OTHER INFORMATION: synthetic primer

<400> SEQUENCE: 43
taccagctca ccaagctcct g                                     21

<210> SEQ ID NO 44
<211> LENGTH: 22
<212> TYPE: DNA
<213> ORGANISM: Artificial
<220> FEATURE:
<223> OTHER INFORMATION: synthetic primer

<400> SEQUENCE: 44
gaaagtccac gctcaccatg tg                                    22

<210> SEQ ID NO 45
<211> LENGTH: 20
<212> TYPE: DNA
<213> ORGANISM: Artificial
<220> FEATURE:
<223> OTHER INFORMATION: synthetic primer

<400> SEQUENCE: 45
gtgtacaaac aggcgcatcc                                       20

<210> SEQ ID NO 46
<211> LENGTH: 21
<212> TYPE: DNA
<213> ORGANISM: Artificial
<220> FEATURE:
<223> OTHER INFORMATION: synthetic primer

<400> SEQUENCE: 46
tcattcttgg tcagagcctc g                                     21

-continued

<210> SEQ ID NO 47
<211> LENGTH: 24
<212> TYPE: DNA
<213> ORGANISM: Artificial
<220> FEATURE:
<223> OTHER INFORMATION: synthetic primer

<400> SEQUENCE: 47
gaggcctgac gagattaata aaga                                      24

<210> SEQ ID NO 48
<211> LENGTH: 21
<212> TYPE: DNA
<213> ORGANISM: Artificial
<220> FEATURE:
<223> OTHER INFORMATION: synthetic primer

<400> SEQUENCE: 48
agggcagatt cttcttggac c                                         21

<210> SEQ ID NO 49
<211> LENGTH: 20
<212> TYPE: DNA
<213> ORGANISM: Artificial
<220> FEATURE:
<223> OTHER INFORMATION: synthetic primer

<400> SEQUENCE: 49
ggagtgacgg aagttgtgct                                           20

<210> SEQ ID NO 50
<211> LENGTH: 20
<212> TYPE: DNA
<213> ORGANISM: Artificial
<220> FEATURE:
<223> OTHER INFORMATION: synthetic primer

<400> SEQUENCE: 50
agctccaagg ggtcggatca                                           20

<210> SEQ ID NO 51
<211> LENGTH: 20
<212> TYPE: DNA
<213> ORGANISM: Artificial
<220> FEATURE:
<223> OTHER INFORMATION: synthetic primer

<400> SEQUENCE: 51
ccctcgattt gaactgccca                                           20

<210> SEQ ID NO 52
<211> LENGTH: 21
<212> TYPE: DNA
<213> ORGANISM: Artificial
<220> FEATURE:
<223> OTHER INFORMATION: synthetic primer

<400> SEQUENCE: 52
tcctttctcg ccacacttgt a                                         21

<210> SEQ ID NO 53
<211> LENGTH: 20
<212> TYPE: DNA
<213> ORGANISM: Artificial
<220> FEATURE:
<223> OTHER INFORMATION: synthetic primer

<400> SEQUENCE: 53
gagcgggatt gagaggatcg                                           20

<210> SEQ ID NO 54
<211> LENGTH: 22
<212> TYPE: DNA
<213> ORGANISM: Artificial
<220> FEATURE:
<223> OTHER INFORMATION: synthetic primer

<400> SEQUENCE: 54
taggatacgt ctggctttga gc                                        22

<210> SEQ ID NO 55
<211> LENGTH: 20
<212> TYPE: DNA
<213> ORGANISM: Artificial
<220> FEATURE:
<223> OTHER INFORMATION: synthetic primer

<400> SEQUENCE: 55
ggagcaccac agtatgggag                                           20

<210> SEQ ID NO 56
<211> LENGTH: 20
<212> TYPE: DNA
<213> ORGANISM: Artificial
<220> FEATURE:
<223> OTHER INFORMATION: synthetic primer

<400> SEQUENCE: 56
atcagcacca ggtttacgcc                                           20

<210> SEQ ID NO 57
<211> LENGTH: 20
<212> TYPE: DNA
<213> ORGANISM: Artificial
<220> FEATURE:
<223> OTHER INFORMATION: synthetic primer

<400> SEQUENCE: 57
cagccacccg agattgagca                                           20

<210> SEQ ID NO 58
<211> LENGTH: 20
<212> TYPE: DNA
<213> ORGANISM: Artificial
<220> FEATURE:
<223> OTHER INFORMATION: synthetic primer

<400> SEQUENCE: 58
tagtagcgac gggcggtgtg                                           20

<210> SEQ ID NO 59
<211> LENGTH: 20
<212> TYPE: DNA
<213> ORGANISM: Artificial
<220> FEATURE:
<223> OTHER INFORMATION: synthetic primer

<400> SEQUENCE: 59
atgcagaaag agataccgc                                            20

```
<210> SEQ ID NO 60
<211> LENGTH: 20
<212> TYPE: DNA
<213> ORGANISM: Artificial
<220> FEATURE:
<223> OTHER INFORMATION: synthetic primer

<400> SEQUENCE: 60
acatctgctg gaaggtggac                                              20

<210> SEQ ID NO 61
<211> LENGTH: 45
<212> TYPE: DNA
<213> ORGANISM: Artificial
<220> FEATURE:
<223> OTHER INFORMATION: AR2 TALEN target site

<400> SEQUENCE: 61
gaacattcct gcctggctga catgtggact ctctgaaatt gttat                  45

<210> SEQ ID NO 62
<211> LENGTH: 25
<212> TYPE: DNA
<213> ORGANISM: Artificial
<220> FEATURE:
<223> OTHER INFORMATION: morpholino targeting upstream of AR CE3

<400> SEQUENCE: 62
acctcattag cctttcaatc cacat                                        25

<210> SEQ ID NO 63
<211> LENGTH: 25
<212> TYPE: DNA
<213> ORGANISM: Artificial
<220> FEATURE:
<223> OTHER INFORMATION: morpholino targeting upstream of AR CE3

<400> SEQUENCE: 63
cactagtaga aatatgcaac attca                                        25

<210> SEQ ID NO 64
<211> LENGTH: 25
<212> TYPE: DNA
<213> ORGANISM: Artificial
<220> FEATURE:
<223> OTHER INFORMATION: morpholino targeting downstream of AR CE3

<400> SEQUENCE: 64
agcattaatt ctctcagtct gttgt                                        25

<210> SEQ ID NO 65
<211> LENGTH: 25
<212> TYPE: DNA
<213> ORGANISM: Artificial
<220> FEATURE:
<223> OTHER INFORMATION: morpholino targeting downstream of AR CE3

<400> SEQUENCE: 65
agcatgacct ggaaagcaaa cgaga                                        25
```